US011867028B2

(12) United States Patent
Bulekbay et al.

(10) Patent No.: US 11,867,028 B2
(45) Date of Patent: Jan. 9, 2024

(54) GAUGE CUTTER AND SAMPLER APPARATUS

(71) Applicant: Saudi Arabian Oil Company, Dhahran (SA)

(72) Inventors: Aslan Bulekbay, Udhailiyah (SA); Graham Hitchcock, Aberdeen (GB); Saad Al-Driweesh, Udhailiyah (SA); Ali J. Aljasim, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/142,855

(22) Filed: Jan. 6, 2021

(65) Prior Publication Data
US 2022/0213761 A1   Jul. 7, 2022

(51) Int. Cl.
| | | |
|---|---|---|
| *E21B 27/00* | (2006.01) | |
| *E21B 37/00* | (2006.01) | |
| *E21B 49/00* | (2006.01) | |
| *G01N 1/08* | (2006.01) | |
| *G01N 33/24* | (2006.01) | |

(52) U.S. Cl.
CPC ............ *E21B 37/00* (2013.01); *E21B 27/005* (2013.01); *E21B 49/00* (2013.01); *G01N 1/08* (2013.01); *G01N 33/24* (2013.01)

(58) Field of Classification Search
CPC ........ E21B 37/00; E21B 27/005; E21B 49/00; G01N 1/08; G01N 33/24
USPC .................................................... 166/250.01
See application file for complete search history.

(56) References Cited

U.S. PATENT DOCUMENTS

| | | |
|---|---|---|
| 381,374 A | 4/1888 | Hine |
| 774,519 A | 11/1904 | Greenaway |
| 2,368,424 A | 1/1945 | Reistle |
| 2,782,857 A | 2/1957 | Clark et al. |

(Continued)

FOREIGN PATENT DOCUMENTS

| | | |
|---|---|---|
| AU | 2013206729 | 4/2015 |
| CN | 104727799 | 6/2015 |

(Continued)

OTHER PUBLICATIONS

PCT International Search Report and Written Opinion in International Appln. No. PCT/US2022/011414, dated Apr. 7, 2022, 14 pages.

(Continued)

*Primary Examiner* — Taras P Bemko
(74) *Attorney, Agent, or Firm* — Fish & Richardson P.C.

(57) ABSTRACT

A wellbore gauge cutter apparatus includes a sampling body defining a central recess extending from an inlet at a first end to an outlet at a second end. The apparatus further includes a gauge cutter connected to the sampling body configured to dislodge particles from an inner wall of a wellbore. The sampling body includes an inner wall defining the central recess, a hollow cylindrical divider having a central aperture, a first flow path defined in the central aperture of the hollow cylindrical divider, a second flow path defined between an outer wall of the hollow cylindrical divider and the inner wall of the sampling body, and a fluid permeable screen arranged in the first flow path or the second flow The fluid permeable screen is configured to collect a portion the particles dislodged by the gauge cutter.

30 Claims, 13 Drawing Sheets

(56) References Cited

U.S. PATENT DOCUMENTS

| | | |
|---|---|---|
| 2,784,787 A | 3/1957 | Matthews et al. |
| 2,890,752 A | 6/1959 | Cron et al. |
| 3,093,192 A | 6/1963 | Allen |
| 3,228,470 A | 1/1966 | Papaila |
| 3,244,230 A | 4/1966 | Sharp |
| 3,285,778 A | 11/1966 | Hauk |
| 3,369,605 A | 2/1968 | Donaldson et al. |
| 3,386,514 A | 6/1968 | Weber |
| 3,497,011 A | 2/1970 | Weber et al. |
| 3,601,197 A | 8/1971 | Ayers et al. |
| 3,656,550 A | 4/1972 | Wagner, Jr. et al. |
| 3,695,356 A | 10/1972 | Argabright et al. |
| 3,866,682 A | 2/1975 | Jones et al. |
| 3,882,937 A | 5/1975 | Robinson |
| 3,937,283 A | 2/1976 | Blauer et al. |
| 3,980,136 A | 9/1976 | Plummer et al. |
| 4,044,833 A | 8/1977 | Volz |
| 4,059,155 A * | 11/1977 | Greer ............... E21B 27/00 166/99 |
| 4,106,562 A | 8/1978 | Barnes et al. |
| 4,157,116 A | 6/1979 | Coulter |
| 4,216,829 A | 8/1980 | Murphy |
| 4,340,405 A | 7/1982 | Steyert |
| 4,476,932 A | 10/1984 | Emery |
| 4,493,875 A | 1/1985 | Beck et al. |
| 4,532,992 A | 8/1985 | Coenen et al. |
| 4,660,643 A | 4/1987 | Perkins |
| 4,705,113 A | 11/1987 | Perkins |
| 4,836,284 A | 6/1989 | Tinker |
| 4,846,277 A | 7/1989 | Khalil et al. |
| 5,018,578 A | 5/1991 | El Rabaa et al. |
| 5,069,283 A | 12/1991 | Mack |
| 5,394,339 A | 2/1995 | Jones |
| 5,394,942 A | 3/1995 | Catania |
| 5,529,123 A | 6/1996 | Carpenter et al. |
| 5,604,184 A | 2/1997 | Ellis et al. |
| 5,613,555 A | 3/1997 | Sorem et al. |
| 5,912,219 A | 6/1999 | Carrie et al. |
| 6,032,539 A | 3/2000 | Liu |
| 6,207,620 B1 | 3/2001 | Gonzalez et al. |
| 6,250,387 B1 | 6/2001 | Carmichael et al. |
| 6,263,970 B1 | 7/2001 | Blanchet |
| 6,347,675 B1 | 2/2002 | Kolle |
| 6,419,730 B1 | 7/2002 | Chavez |
| 6,585,046 B2 | 7/2003 | Neuroth et al. |
| 6,729,409 B1 | 5/2004 | Gupta et al. |
| 6,766,856 B1 | 7/2004 | McGee |
| 6,776,231 B2 | 8/2004 | Allen |
| 6,776,235 B1 | 8/2004 | England |
| 6,883,605 B2 | 4/2005 | Arceneaux et al. |
| 6,988,552 B2 | 1/2006 | Wilson et al. |
| 7,001,872 B2 | 2/2006 | Pyecroft et al. |
| 7,044,220 B2 | 5/2006 | Nguyen et al. |
| 7,063,150 B2 | 6/2006 | Slabaugh et al. |
| 7,134,497 B1 | 11/2006 | Chatterji et al. |
| 7,210,528 B1 | 5/2007 | Brannon et al. |
| 7,252,146 B2 | 8/2007 | Slabaugh et al. |
| 7,255,169 B2 | 8/2007 | van Batenburg et al. |
| 7,281,580 B2 | 10/2007 | Parker et al. |
| 7,281,581 B2 | 10/2007 | Nyuyen et al. |
| 7,334,635 B2 | 2/2008 | Nguyen |
| 7,334,636 B2 | 2/2008 | Nguyen |
| 7,422,060 B2 | 9/2008 | Hammami et al. |
| 7,424,911 B2 | 9/2008 | McCarthy et al. |
| 7,426,961 B2 | 9/2008 | Stephenson et al. |
| 7,434,623 B2 | 10/2008 | Von Gynz-Rekowski |
| 7,451,812 B2 | 11/2008 | Cooper et al. |
| 7,472,751 B2 | 1/2009 | Brannon et al. |
| 7,516,787 B2 | 4/2009 | Kaminsky |
| 7,571,767 B2 | 8/2009 | Parker et al. |
| 7,581,590 B2 | 9/2009 | Lesko et al. |
| 7,610,962 B2 | 11/2009 | Fowler |
| 7,647,971 B2 | 1/2010 | Kaminsky |
| 7,677,317 B2 | 3/2010 | Wilson |
| 7,735,548 B2 | 6/2010 | Cherewyk |
| 7,767,628 B2 | 8/2010 | Kippie et al. |
| 7,803,740 B2 | 9/2010 | Bicerano et al. |
| 7,861,772 B2 * | 1/2011 | Blair ............... E21B 37/00 166/99 |
| 7,918,277 B2 | 4/2011 | Brannon et al. |
| 8,002,038 B2 | 8/2011 | Wilson |
| 8,006,760 B2 | 8/2011 | Fleming et al. |
| 8,066,068 B2 | 11/2011 | Lesko et al. |
| 8,100,190 B2 | 1/2012 | Weaver |
| 8,104,537 B2 | 1/2012 | Kaminsky |
| 8,119,576 B2 | 2/2012 | Reyes et al. |
| 8,127,850 B2 | 3/2012 | Brannon et al. |
| 8,205,675 B2 | 6/2012 | Brannon et al. |
| 8,408,305 B2 | 4/2013 | Brannon et al. |
| 8,490,700 B2 | 7/2013 | Lesko et al. |
| 8,584,755 B2 | 11/2013 | Willberg et al. |
| 8,636,065 B2 | 1/2014 | Lesko et al. |
| 8,727,008 B2 | 5/2014 | Krpec |
| 8,757,259 B2 | 6/2014 | Lesko et al. |
| 8,763,699 B2 | 7/2014 | Medvedev et al. |
| 8,936,083 B2 | 1/2015 | Nguyen |
| 8,985,213 B2 | 3/2015 | Saini et al. |
| 9,080,440 B2 | 7/2015 | Panga et al. |
| 9,085,727 B2 | 7/2015 | Litvinets et al. |
| 9,095,799 B1 | 8/2015 | Packard |
| 9,097,094 B1 | 8/2015 | Frost |
| 9,109,429 B2 | 8/2015 | Xu et al. |
| 9,114,332 B1 | 8/2015 | Liu |
| 9,181,789 B2 | 11/2015 | Nevison |
| 9,328,282 B2 | 5/2016 | Li |
| 9,447,673 B2 | 9/2016 | Medvedev et al. |
| 9,523,268 B2 | 12/2016 | Potapenko et al. |
| 9,670,764 B2 | 6/2017 | Lesko et al. |
| 9,725,639 B2 | 8/2017 | Vo et al. |
| 9,725,645 B2 | 8/2017 | Monastiriotis et al. |
| 9,757,796 B2 | 9/2017 | Sherman et al. |
| 9,777,562 B2 | 10/2017 | Lastra et al. |
| 9,816,365 B2 | 11/2017 | Nguyen et al. |
| 9,845,670 B2 | 12/2017 | Surjaatmadja et al. |
| 9,863,230 B2 | 1/2018 | Litvinets et al. |
| 9,863,231 B2 | 1/2018 | Hull |
| 9,902,898 B2 | 2/2018 | Nelson et al. |
| 9,903,010 B2 | 2/2018 | Doud et al. |
| 9,909,404 B2 | 3/2018 | Hwang et al. |
| 9,945,220 B2 | 4/2018 | Saini et al. |
| 9,976,381 B2 | 5/2018 | Martin et al. |
| 9,995,125 B2 | 6/2018 | Madasu et al. |
| 10,001,769 B2 | 6/2018 | Huang et al. |
| 10,012,054 B2 | 7/2018 | Ciglenec |
| 10,030,495 B2 | 7/2018 | Litvinets et al. |
| 10,047,281 B2 | 8/2018 | Nguyen et al. |
| 10,077,396 B2 | 9/2018 | Nguyen et al. |
| 10,087,364 B2 | 10/2018 | Kaufman et al. |
| 10,100,245 B1 | 10/2018 | Bulekbay et al. |
| 10,208,239 B2 | 2/2019 | Ballard |
| 10,352,125 B2 | 7/2019 | Frazier |
| 10,421,897 B2 | 9/2019 | Skiba et al. |
| 10,450,839 B2 | 10/2019 | Bulekbay et al. |
| 10,508,517 B2 | 12/2019 | Bulekbay et al. |
| 10,550,314 B2 | 2/2020 | Liang et al. |
| 10,655,443 B2 | 5/2020 | Gomma et al. |
| 10,836,956 B2 | 11/2020 | Bulekbay et al. |
| 10,858,578 B2 | 12/2020 | Bulekbay et al. |
| 10,883,042 B2 | 1/2021 | Bulekbay |
| 2002/0043507 A1 | 4/2002 | McCulloch |
| 2004/0173244 A1 | 9/2004 | Strothoff et al. |
| 2005/0097911 A1 | 5/2005 | Revellat |
| 2005/0126784 A1 | 6/2005 | Dalton |
| 2005/0137094 A1 | 6/2005 | Weaver et al. |
| 2005/0194147 A1 | 9/2005 | Metcalf et al. |
| 2006/0035808 A1 | 2/2006 | Ahmed et al. |
| 2006/0073980 A1 | 4/2006 | Brannon et al. |
| 2006/0144619 A1 | 7/2006 | Storm |
| 2006/0157249 A1 * | 7/2006 | Reynolds ............... E21B 27/005 166/99 |
| 2007/0012437 A1 | 1/2007 | Clingman et al. |
| 2007/0215355 A1 | 9/2007 | Shapovalov |

(56) References Cited

U.S. PATENT DOCUMENTS

| | | |
|---|---|---|
| 2008/0135242 A1 | 6/2008 | Lesko |
| 2008/0149329 A1 | 6/2008 | Cooper |
| 2008/0153718 A1 | 6/2008 | Heidenfelder et al. |
| 2008/0223579 A1 | 9/2008 | Goodwin |
| 2009/0044945 A1 | 2/2009 | Willberg et al. |
| 2009/0151944 A1 | 6/2009 | Fuller et al. |
| 2009/0298720 A1 | 12/2009 | Nguyen et al. |
| 2010/0043823 A1 | 2/2010 | Lee |
| 2010/0282468 A1 | 11/2010 | Willberg et al. |
| 2010/0323933 A1 | 12/2010 | Fuller |
| 2012/0018143 A1 | 1/2012 | Lembcke |
| 2012/0097392 A1 | 4/2012 | Reyes et al. |
| 2012/0112546 A1 | 5/2012 | Culver |
| 2012/0118571 A1 | 5/2012 | Zhou |
| 2012/0125618 A1 | 5/2012 | Willberg |
| 2012/0247764 A1 | 10/2012 | Panga |
| 2012/0305247 A1 | 12/2012 | Chen et al. |
| 2013/0032549 A1 | 2/2013 | Brown et al. |
| 2013/0161003 A1 | 6/2013 | Mikhailovich et al. |
| 2013/0260649 A1 | 10/2013 | Thomson |
| 2013/0312977 A1 | 11/2013 | Lembcke |
| 2013/0341027 A1 | 12/2013 | Xu et al. |
| 2014/0000899 A1 | 1/2014 | Nevison |
| 2014/0131040 A9 | 5/2014 | Panga |
| 2014/0144633 A1 | 5/2014 | Nguyen |
| 2014/0144634 A1 | 5/2014 | Nguyen |
| 2014/0144635 A1 | 5/2014 | Nguyen |
| 2014/0290943 A1 | 10/2014 | Ladva |
| 2014/0296113 A1 | 10/2014 | Reyes |
| 2014/0352954 A1 | 12/2014 | Lakhtychkin et al. |
| 2015/0047846 A1 | 2/2015 | Oort |
| 2015/0071750 A1 | 3/2015 | Foster |
| 2015/0083420 A1 | 3/2015 | Gupta et al. |
| 2015/0211346 A1 | 7/2015 | Potapenko |
| 2015/0259593 A1 | 9/2015 | Kaufman et al. |
| 2015/0369028 A1 | 12/2015 | Potapenko |
| 2016/0153274 A1 | 6/2016 | Hull et al. |
| 2016/0208591 A1 | 7/2016 | Weaver et al. |
| 2016/0215604 A1 | 7/2016 | Potapenko et al. |
| 2016/0319189 A1 | 11/2016 | Dusterhoft |
| 2016/0347994 A1 | 12/2016 | Purdy et al. |
| 2017/0066962 A1 | 3/2017 | Ravi et al. |
| 2017/0121593 A1 | 5/2017 | Pantsurkin |
| 2017/0138190 A1 | 5/2017 | Elkatatny et al. |
| 2018/0202278 A1 | 7/2018 | Nelson et al. |
| 2018/0230361 A1 | 8/2018 | Foster |
| 2018/0244981 A1 | 8/2018 | Panga et al. |
| 2018/0328156 A1 | 11/2018 | Slater |
| 2018/0334612 A1 | 11/2018 | Bulekbay et al. |
| 2019/0055818 A1 | 2/2019 | Bulekbay |
| 2019/0264095 A1 | 8/2019 | Qu et al. |
| 2019/0323320 A1 | 10/2019 | Bulekbay et al. |
| 2019/0345377 A1 | 11/2019 | Haque et al. |
| 2020/0003053 A1* | 1/2020 | Pelletier .................. E21B 47/07 |

FOREIGN PATENT DOCUMENTS

| | | |
|---|---|---|
| CN | 102777138 | 1/2016 |
| EP | 306546 | 3/1989 |
| FR | 2920435 | 8/2007 |
| GB | 239998 | 9/1925 |
| GB | 2063840 | 6/1981 |
| WO | WO 1992019838 | 11/1992 |
| WO | WO 2006076330 | 7/2006 |
| WO | WO 2006108161 | 10/2006 |
| WO | WO 2016108161 | 10/2006 |
| WO | WO 2009018536 | 2/2009 |
| WO | WO 2010026553 | 3/2010 |
| WO | WO 2015012818 | 1/2015 |
| WO | WO 2015071750 | 5/2015 |
| WO | WO 2016032578 | 3/2016 |
| WO | WO 2017040553 | 3/2017 |
| WO | WO 2017164878 | 9/2017 |
| WO | WO 2018106121 | 6/2018 |

OTHER PUBLICATIONS

"Echo Dissolvable Fracturing Plug," EchoSeries, Dissolvable Fracturing Plugs, Gryphon Oilfield Solutions, Aug. 2018, 1 page.

"Terv Alloy Degradable Magnesium Alloys," Terves Engineered Response, Engineered for Enhanced Completion Efficiency, Feb. 2018, 8 pages.

Alipour-Kivi et al., "Automated Liquid Unloading in Low-Pressure Gas Wells Using Intermittent and Distributed Heating of Wellbore Fluid," SPE 100650, Society of Petroleum Engineers (SPE), presented at the SPE Western Regional/AAPG Pacific Section/GSA Cordilleran Section Joint Meeting, 2006, 6 pages.

Ansari et al., "Innovative Planning and Remediation Techniques for Restoring the Well Integrity by Curing High Annulus-B Pressure and Zonal Communications," IPTC-18894-MS, International Petroleum Technology Conference (IPTC), presented at the International Petroleum Technology Conference, Nov. 14-16, 2016, 24 pages.

Barree et al., "Realistic Assessment of Proppant Pack Conductivity for Material Selection," SPE- 84306-MS, Society of Petroleum Engineers (SPE), presented at the Annual Technical Conference, Oct. 5-8, 2003, 12 pages.

Clifton, "Modeling of In-Situ Stress Change Due to Cold Fluid Injection," SPE 22107, Society of Petroleum Engineers (SPE), presented at the International Arctic Technology Conference, May 29-31, 1991, 13 pages.

Corona et al., "Novel Washpipe-Free ICD Completion With Dissolvable Material," OTC-28863-MS, Offshore Technology Conference (OTC), presented at the Offshore Technology Conference, Apr. 30-May 3, 2018, 10 pages.

Gil et al., "Wellbore Cooling as a Means to Permanently Increase Fracture Gradient," SPE Annual Technical Conference and Exhibition, San Antonio, Texas, Sep. 24-27, 2006, published Jan. 1, 2006, 9 pages.

Gillard et al., "A New Approach to Generating Fracture Conductivity," SPE-135034-MS, Society of Petroleum Engineers (SPE), presented at the SPE Annual Technical Conference and Exhibition held in Florence, Italy, Sep. 20-22, 2010, 13 pages.

glossary.oilfield.slb.com [online], "Underbalance," retrieved on Apr. 12, 2019, retrieved from URL http://www.glossary.oilfield.slb.com/Terms/u/underbalance.aspx, 1 pages.

Gomaa et al., "Acid Fracturing: The Effect of Formation Strength on Fracture Conductivity," SPE 119623, Society of Petroleum Engineers (SPE), presented at the SPE Hydraulic Fracturing Technology Conference, Jan. 2009, 18 pages.

Gomaa et al., "Computational Fluid Dynamics Applied to Investigate Development and Optimization of Highly Conductive Channels within the Fracture Geometry," SPE-179143-MS, Society of Petroleum Engineers (SPE), presented at the SPE Hydraulic Fracturing Technology Conference, Texas, Feb. 9-11, 2016, 18 pages.

Gomaa et al., "Improving Fracture Conductivity by Developing and Optimizing a Channels Within the Fracture Geometry: CFD Study," SPE-178982-MS, Society of Petroleum Engineers (SPE), presented at the SPE International conference on Formation Damage Control in Layfayette, Feb. 24-26, 2016, 25 pages.

hub.globalccsinstitute.com [online], "2.1 The Properties of CO2," available on or before Oct. 22, 2015, via Internet Archive: Wayback Machine URL <https://hub.globalccsinstitute.com/publications/hazard-analysis-offshore-carbon-capture-platforms-and-offshore-pipelines/21-properties-co2>, 12 pages.

Jensen, "Thermally induced hydraulic fracturing of cold water injectors," WPC-26154, World Petroleum Conference (WPC), 14th World Petroleum Congress, May 29-Jun. 1, 1994, 2 pages.

Kern et al., "Propping Fractures with Aluminum Particles," SPE-1573-G-PA, Society of Petroleum Engineers (SPE), Journal of Petroleum Technology, Jun. 1961, 13:6 (583-589), 7 pages.

Masa and Kuba, "Efficient use of compressed air for dry ice blasting," Journal of Cleaner Production, 111:A, Jan. 2016, 9 pages.

Mayerhofer et al., "Proppants? We Don't Need No Proppants," SPE-38611, Society of Petroleum Engineers (SPE), presented at the SPE Annual Technical Conference and Exhibition, 457-464, Oct. 5, 1997, 8 pages.

Meyer et al., "Theoretical Foundation and Design Formulae for Channel and Pillar Type Propped Fractures—A Method to Increase

(56) References Cited

OTHER PUBLICATIONS

Fracture Conductivity," SPE-170781-MS, Society of Petroleum Engineers (SPE), presented at SPE Annual Technical Conference and Exhibition, Amsterdam, The Netherlands, Oct. 27-29, 2014, 25 pages.

Mueller et al., "Stimulation of Tight Gas Reservoir using coupled Hydraulic and CO2 Cold-frac Technology," SPE 160365, Society of Petroleum Engineers (SPE), presented at the SPE Asia Pacific Oil and Gas Conference and Exhibition, Oct. 22-24, 2012, 7 pages.

Palisch et al., "Determining Realistic Fracture Conductivity and Understanding its Impact on Well Performance—Theory and Field Examples," SPE-106301-MS, Society of Petroleum Engineers (SPE), presented at the 2007 Hydraulic Fracturing Technology Conference, College Station, Texas, Jan. 29-31, 2007, 13 pages.

Praxair, "Carbon Dioxide, Solid or Dry Ice, Safety Data Sheet P-4575," Praxair, Jan. 1, 1997, 7 pages.

princeton.edu [online], "Bernoulli's Equation," available on or before Jul. 24, 1997, via Internet Archive: Wayback Machine URL <https://www.princeton.edu/~asmits/Bicycle_web/Bernoulli.html>, 5 pages.

Singh et al., "Introduction to an Effective Workover Method to Repair Causing Leak," SPE-194654-MS, Society of Petroleum Engineers (SPE), presented at the SPE Oil and Gas India Conference and Exhibition, Apr. 9-11, 2019, 7 pages.

Soreide et al., "Estimation of reservoir stress effects due to injection of cold fluids: an example from NCS," ARMA 14-7394, American Rock Mechanics Association, presented at the 48th US Rock mechanics/Geomechanics Symposium, Jun. 1-4, 2014, 7 pages.

Takahashi et al., "Degradation Study on Materials for Dissolvable Frac Plugs," URTEC-2901283-MS, Unconventional Resources Technology Conference (URTC), presented at the SPE/AAPG/SEG Unconventional Resources Technology Conference, Jul. 23-25, 2018, 9 pages.

Tinsley and Williams, "A new method for providing increased fracture conductivity and improving stimulation results," SPE-4676-PA, Society of Petroleum Engineers (SPE), Journal of Petroleum Technology, 27:11 (1317-1325), 1975, 7 pages.

Van Poollen et al., "Hydraulic Fracturing—Fracture Flow Capacity vs Well Productivity," SPE-890-G, Society of Petroleum Engineers (SPE), Petroleum Transactions AIME, 213: 91-95, 1958, 5 pages.

Van Poollen, "Productivity vs Permeability Damage in Hydraulically Produced Fractures," SPE-906-2-G, Society of Petroleum Engineers (SPE), presented at Drilling and Production Practice, New York, New York, Jan. 1957, 8 pages.

Vincent, "Examining our Assumptions—Have oversimplifications jeopardized our ability to design optimal fracture treatments," SPE-119143-MS, Society of Petroleum Engineers (SPE), presented at the SPE Hydraulic Fracturing Technology Conference, The Woodlands, Jan. 19-21, 2009, 51 pages.

Vincent, "Five Things you Didn't Want to Know about Hydraulic Fractures," ISRM-ICHF-2013-045, presented at the International Conference for Effective and Sustainable Hydraulic Fracturing, an ASRM specialized Conference, Australia, May 20-22, 2013, 14 pages.

Weinstein, "Cold Waterflooding a Warm Reservoir," SPE 5083, Society of Petroleum Engineers (SPE), presented at the 49th Annual Fall Meeting of the Society of Petroleum Engineers of AIME, Oct. 6-9, 1974, 16 pages.

Williams et al., "Acidizing Fundamentals," Society of Petroleum Engineers of AIME, Jan. 1979, 131 pages.

Yu et al., "Chemical and Thermal Effects on Wellbore Stability of Shale Formations," SPE 71366, Society of Petroleum Engineers (SPE), presented at the 2001 SPE Annual Technical Conference and Exhibition, Sep. 30-Oct. 3, 2001, 11 pages.

* cited by examiner

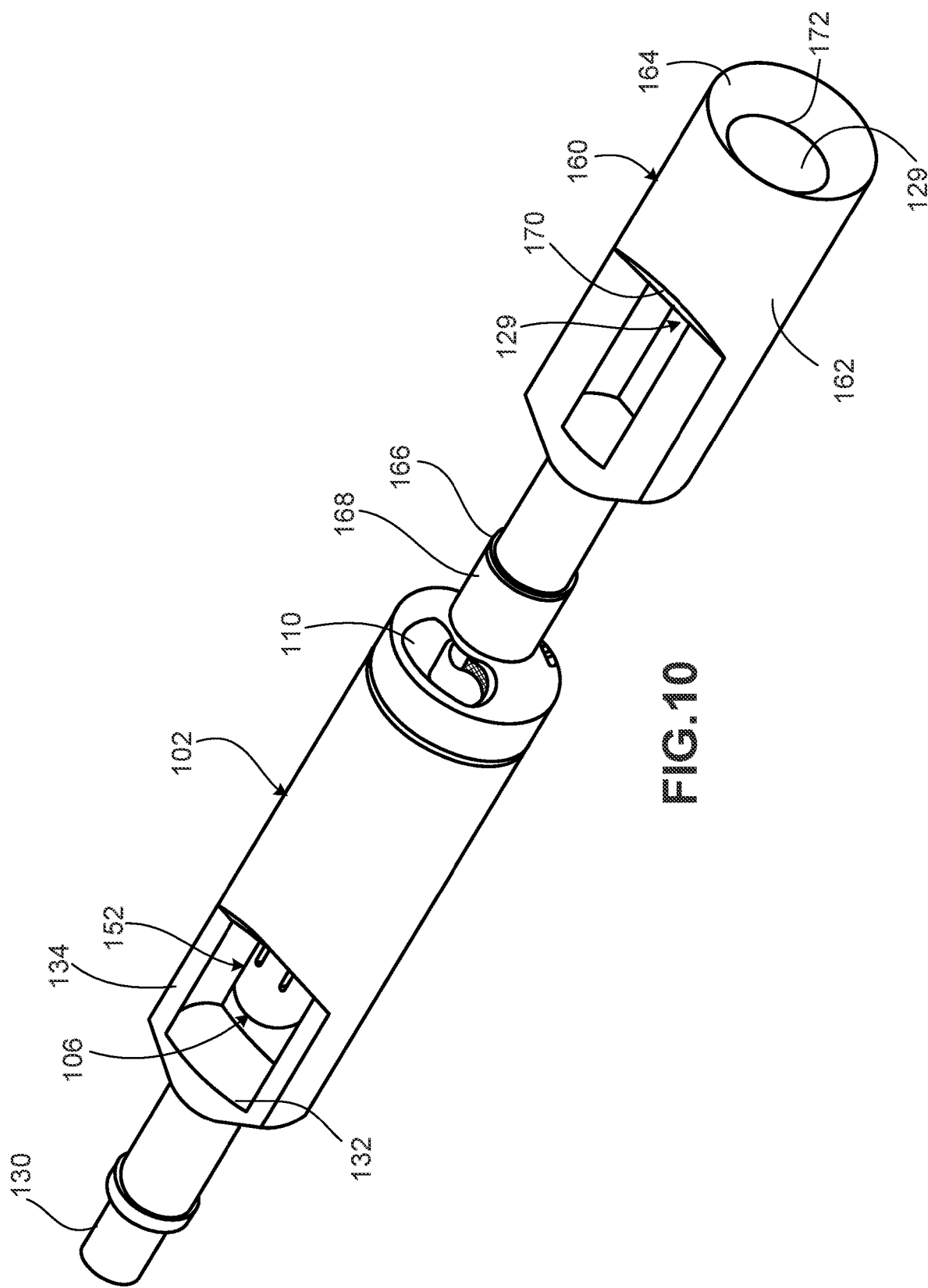

GAUGE CUTTER AND SAMPLER APPARATUS

TECHNICAL FIELD

The present disclosure relates to a wellbore tool for gauging a wellbore and sampling particles in the wellbore.

BACKGROUND

Gauge cutters are commonly used in petroleum industry for ensuring accessibility of tubing/casing/liner prior to running any other sub-surface tools inside the well. A gauge cutter is a tool with a round, open-ended bottom which is milled to an accurate size. Large openings above the bottom of the tool allow for fluid bypass while running in the hole. Often a gauge ring will be the first tool run on a slickline operation. A gauge cutter can also be used to remove light paraffin that may have built up in the casing and drift runs. A sand bailer can be used to sample or remove paraffin wax, mechanical debris, formation sand, and/or scale.

SUMMARY

In certain aspects, a wellbore gauge cutter apparatus includes a sampling body defining a central recess extending from an inlet at a first end of the sampling body to an outlet at a second end of the sampling body. The wellbore gauge cutter apparatus also includes a gauge cutter connected to the sampling body. The gauge cutter is configured to dislodge particles from an inner wall of a wellbore. The sampling body has an inner wall defining the central recess and a hollow cylindrical divider having a central aperture. The hollow cylindrical divider is arranged concentrically within the central recess of the sampling body. The sampling body also includes a first flow path defined in the central aperture of the hollow cylindrical divider, a second flow path defined between an outer wall of the hollow cylindrical divider and the inner wall of the sampling body, and a fluid permeable screen arranged in either a first flow path or the second flow path. The fluid permeable screen is configured to collect a portion the particles dislodged by the gauge cutter.

In some cases, the first flow path and the second flow path extend from the inlet to the outlet.

In some embodiments, a shape of the gauge cutter and the shape of the sampling body match.

In some apparatuses, the first and second flow path of the sampling body are merged between the inlet and an uphole end of the hollow cylindrical divider.

In some cases, the first flow path is larger than the second flow path, wherein the screen is arranged in the second flow path.

In some embodiments, the second flow path of the sampling body is larger than the first flow path of the sampling body. The fluid permeable screen may be arranged in the first flow path.

In some apparatuses, the outlet of the sampling body is fluidly connected with an inlet of the gauge cutter.

In some embodiments, the portion of the particles is 100 grams by weight.

Some fluid permeable screens are removable from the sampling body.

In certain aspects, a wellbore gauge cutter apparatus includes an uphole end, a downhole end, and a cylindrical body. The cylindrical body defines a central recess extending from a first end of the cylindrical body to a second end of the cylindrical body. The wellbore gauge cutter apparatus also includes a cutter blade connected to the second end of the cylindrical body and a sample collector permeable to fluids. The sample collector is configured to retain particles. The sample collector arranged in the central recess of the cylindrical body. The central recess of the cylindrical body has a first cross-section having a first area, wherein the sample collector has a second-cross section having a second area, wherein the second area is less than the first area.

In some cases, the cylindrical body includes a first beam extending from first end of the cylindrical body to a connector. The cylindrical body can include a second beam extending from first end of the cylindrical body to a connector. In some cases, the first beam and second beam define an inlet and the inlet is in fluid communication the central recess of the cylindrical body.

Some sample collectors have a volume of about 0.3 liters to about 1 liter.

The sampling collector can include a membrane permeable to fluids. In some cases, the sampling collector is releasable from the cylindrical body. Some sample collectors are annularly shaped. In some embodiments, the first cross-section is circular. The cutter blade can be a gauge cutter.

In certain aspects, a method includes cutting, by a gauge cutter during a downhole motion of a gauge cutter apparatus through a casing of a wellbore, a material from internal walls of the casing of the wellbore such that particles of the material are suspended in fluid. The method also includes, after cutting the material from the internal walls, separating, by sampling body mechanically connected to the gauge cutter during an uphole motion of the gauge cutter apparatus through the casing of the wellbore, the fluid with the suspended particles in the sampling body into a first flow path of the sampling body or a second flow path of the sampling body. A majority of the fluid entering the sampling body is separated into the first flow path of the sampling body. The method also includes collecting a sample of the particles with a sample collector arranged in the second flow path of the sampling body.

Some methods include removing the sample collector from the sampling body to access the collected particles.

In some cases, the method includes analyzing the particles using an x-ray diffraction test, an acid test, or both an x-ray diffraction test and an acid test.

In some embodiments, the first and second flow paths extend to an outlet of the gauge cutter apparatus.

The wellbore gauge cutting apparatus samples the debris and particles dislodged by the wellbore gauge cutter apparatus in a single trip. The wellbore gauge cutter apparatus may increase the speed of cutting and debris sampling and may reduce errors by eliminating the need to switch tools between runs. Further, the sampling body protects the collected sample during cutting and transportation to the surface so that the samples may be accurately analyzed. Analyzing the sample can also determine the chemical compositions and natures of the particle. A fit-for-purpose removal well intervention can be designed around the chemical composition.

The details of one or more implementations are set forth in the accompanying drawings and the description below. Other features, objects, and advantages will be apparent from the description and drawings, and from the claims.

DESCRIPTION OF DRAWINGS

FIG. 10 is a perspective view of a gauge cutter apparatus having a sampling body and a gauge cutter axially spaced from the sampling body.

Like reference symbols in the various drawings indicate like elements.

DETAILED DESCRIPTION

The gauge cutter apparatus may be used in wellbores to dislodge, scrape, or clean debris from the inner walls of a wellbore casing, or other tubular structure in the wellbore. The apparatus includes a sampling body with sampling collectors or screens that are permeable to fluids. The sampling collectors retain a portion of the particles suspended in the fluid for later analysis at the surface. In use, the gauge cutter apparatus undergoes running-in-hole (RIH) operation to dislodge debris from an internal wall of the casing. The debris, in the form of particles, is suspended in a fluid in the casing. The wellbore gauge cutter apparatus then undergoes pulling out of hole (POOH) operation in which a portion of the fluid in the casing flows through the sample collector or screen. The other portion of the fluid with suspended particles in the casing flows through the gauge cutter apparatus but does not interact with the sampling collector or screen. At the surface, the sampling collector can be separated from the sampling body to access the collected sample for further analysis.

The wellbore gauge cutter apparatus samples the debris and particles dislodged by the wellbore gauge cutter apparatus in a single trip. The gauge cutter apparatus may increase the speed of cutting and debris sampling and may reduce errors by eliminating the need to switch tools between runs. Further, the sampling body protects the collected sample during cutting and transportation to the surface so that the samples may be accurately analyzed. In some instances, the sampling body holds the collected particles in order of dislodgment, so that the sample deepest in the sample collector can be inferred to have been collected farthest from the surface. In other instances the sample deepest the sample collected can be inferred to have been collected nearest to the surface. Knowing the axial position of collected particles relative to the axial position of other collected particles can be beneficial in determining the type and severity of the debris formed on the casing. Analyzing the sample can also determine the chemical compositions and natures of the particle. A fit-for-purpose removal well intervention can be designed around the chemical composition and, if applicable, the positions of the particles relative to the wellbore.

Figure 1:
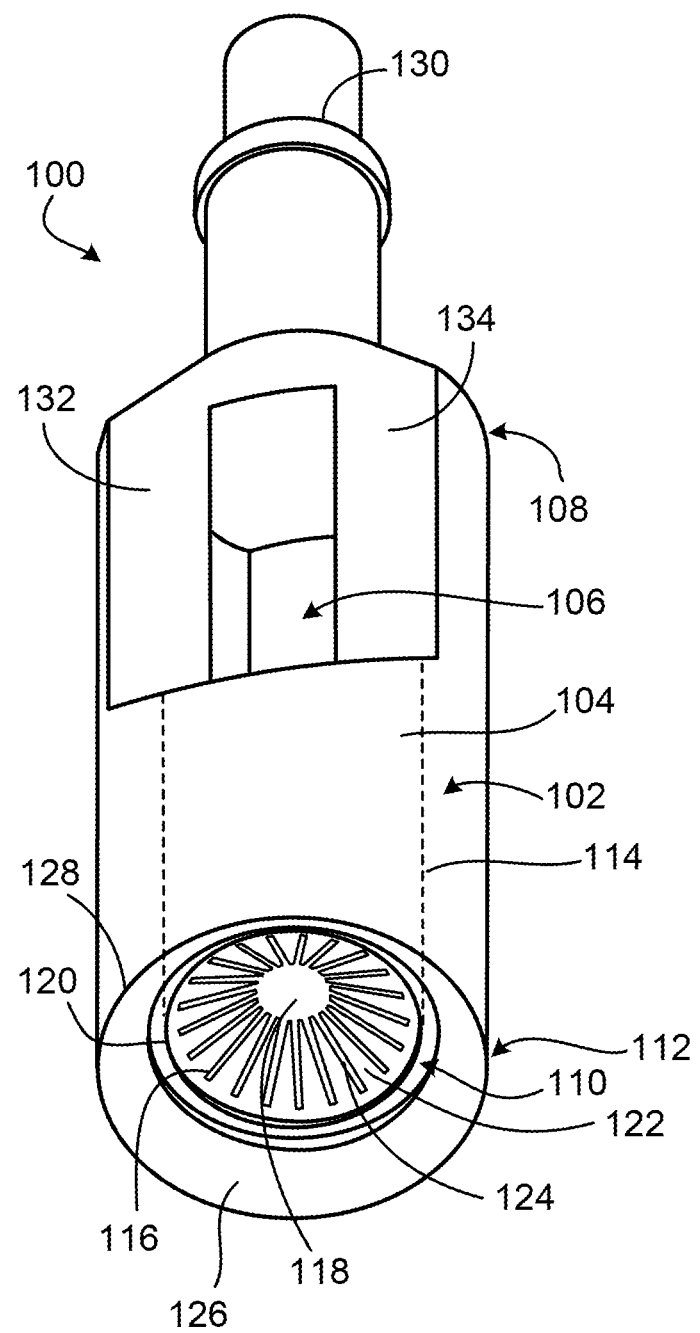
FIG. 1 is a perspective view of a gauge cutter apparatus with a removable sampling body.

FIG. 1 is a perspective view of a wellbore gauge cutter apparatus 100 with a removable sampling body 102. The sampling body (cylindrical body) 102 defines a central recess 104 that extends from an inlet 106 at the first end (uphole end) 108 of the sampling body 102 to an outlet 110 at a second end (down hole) 112 of the sampling body 102. The inlet 106 and outlet 110 are open to the environment in which the wellbore gauge cutter apparatus 100 is located. The inlet 106 and outlet 110 are in fluid connection by the central recess 104. The sampling body 102 further includes an inner wall 114 that defines the central recess 104. The inner wall 114 is shown as cylindrical, however, the inner wall may have other shapes, for example frustoconical, square, rectangular, elliptical, or polygonal.

The wellbore gauge cutter apparatus 100 further includes a sample collector 116 (e.g., a screen) arranged at an axial position in the central recess 104 of the sampling body 102. The sample collector 116 is arranged at the outlet 110 of the central recess 104, however, other sample collectors may be arranged at the inlet of the sample body, or at any other location in the central recess between the inlet of the sampling body and the outlet of the sampling body. The sample collector 116 is permeable to fluids and is configured to retain particles, solids, and/or debris. The sample collector can be or include a screen, (fluid) divider, permeable partition, flexible membrane, rigid membrane, filter, fabric mesh, wire mesh, or a combination thereof. The sample collector can be entirely rigid, entirely flexible, or both rigid and flexible at different portions of the sample collector. In some instances, the sample collector is made of an elastic, stretchable material. The sample collector can be made of plastic, metal, fabric, polymer, elastomers, or combinations thereof.

The sample collector 116 is annularly shaped such that an opening 118 is defined in the center of the sample collector 116 and a base 120 connects or mounts the sample collector 116 to the inner wall 114. The sample collector 116 includes prongs 122 separated by slots 124, that extend from the base 120 and terminate at the opening 118. The slots 124 are open spaces though which fluid, and particle of smaller than a predetermined size, may flow. The width of the slot is about 0.1 mm to about 15 mm (e.g., 0.5 mm to about 10 mm). The width of the slots may be adjusted to account for a larger or a smaller particle size. The prongs 122 retain particles larger than the width of the slots 124 when fluid containing particles flows through the sample collector 116. The sample collector 116 retains particles larger than 1 mm, however, the sample collector can be formed to retain particle sized from at least 0.1 mm to 12 mm. The sample collector 116 can be disconnected from the inner wall 114 of the central recess 104, and removed from the sampling body 102 via the outlet of the sampling body 102, described further with reference to FIG. 5.

The wellbore gauge cutter apparatus 100 further includes a gauge cutter (cutting blade) 126 configured to dislodge debris from an internal wall of a wellbore. The gauge cutter extends (downhole) from on the second end 112 of the sampling body 102 so that a free end 128 of the gauge cutter, scrapes, cuts, or scours the inner wall of the wellbore. The gauge cutter 126 defines an aperture 129 that extends through the gauge cutter 126. The aperture 129 and the outlet 110 are aligned such that the aperture 129 and outlet 110 are in fluid communication. In use, the dislodged debris is suspended in fluid in the form of debris particles. A portion of the particles can be collected by the sample collector 116. Some gauge cutters are integrally formed with the sampling body or are connected to the sampling body (e.g., by mounting or releasable attachment).

The gauge cutter 126 is the same shape and size as the sampling body 102, such that both are cylindrically shaped and have the same diameter. Some gauge cutters are shaped differently from the sampling body, in that the gauge cutter may have a larger diameter or may mirror the shape of the well bore casing to form a close fit with the casing. In some instances, the gauge cutter is detachable from the second end of the sampling body and replaceable by a different gauge cutter. The connection between the gauge cutter and the sampling body may be a snap fit connection, magnetic connection, bolted connection, tongue and groove connection, or any other mechanical connection known in the art. Such an embodiment is described in further detail with reference to FIGS. 10 and 11.

The wellbore gauge cutter apparatus 100 includes a connector 130 that connects the wellbore gauge cutter apparatus 100 to a slick line, wireline, or coiled tubing. A first beam 132 and a second beam 134 of the sampling body 102 arranged at the first end 108 of the sampling body 102 each extend to the connector 130. The beams 132, 134 at least partially define the inlet 106 of the sampling body 102. The inlet 106 formed by the beams 132, 134 is in fluid communication with aperture 129 of the gauge cutter 126 via the outlet 110 defined at the second end 112 of the sampling body 102 and the central recess 104.

Figure 2:
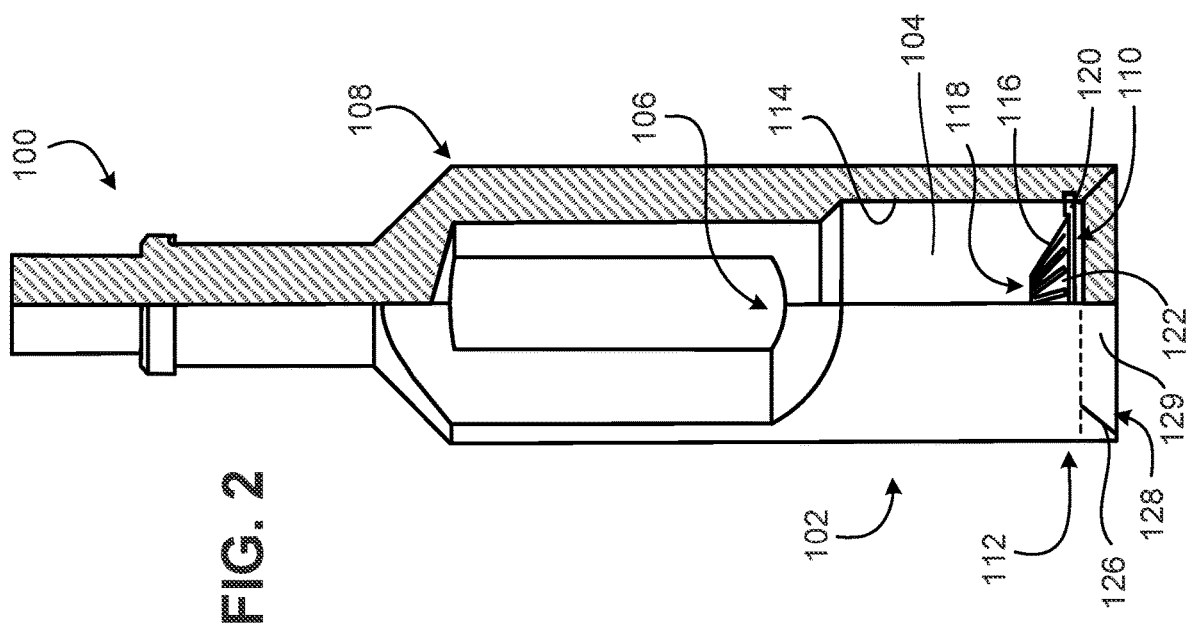
FIG. 2 is a partial front cross-sectional view of the gauge cutter apparatus of FIG. 1.

FIG. 2 is a partial cross-sectional view of the gauge cutter apparatus 100. The central recess 104 of the sampling body 102 is exposed to view the central recess 104.

Figure 3:
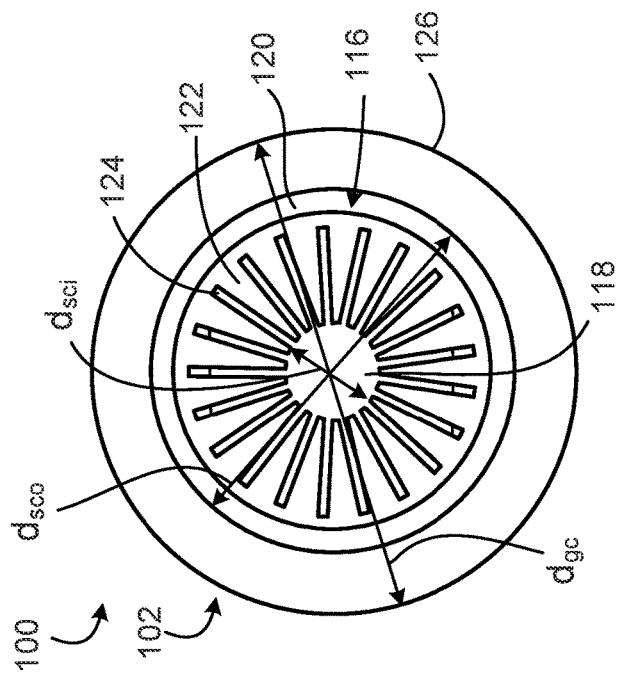
FIG. 3 is a bottom view of an outlet of the wellbore gauge cutter apparatus of FIG. 1.

FIG. 3 is a bottom view of the outlet 110 of sampling body 102 of the wellbore gauge cutter apparatus 100 as viewed through the aperture 129 of the gauge cutter 126. The sample collector 116 has an outer diameter $d_{sco}$ defined at the base 120 an inner diameter $d_{sci}$ which defines the opening 118, and a cross section having an area $A_{sc}$. The cross sectional area $A_{sc}$ of the sample collector 116 is generally annular, however, the cross section of the sample collector may be a different shape, for example, a circle, crescent, half circle, square, triangular, polygonal, or any other shape.

Figure 4A:
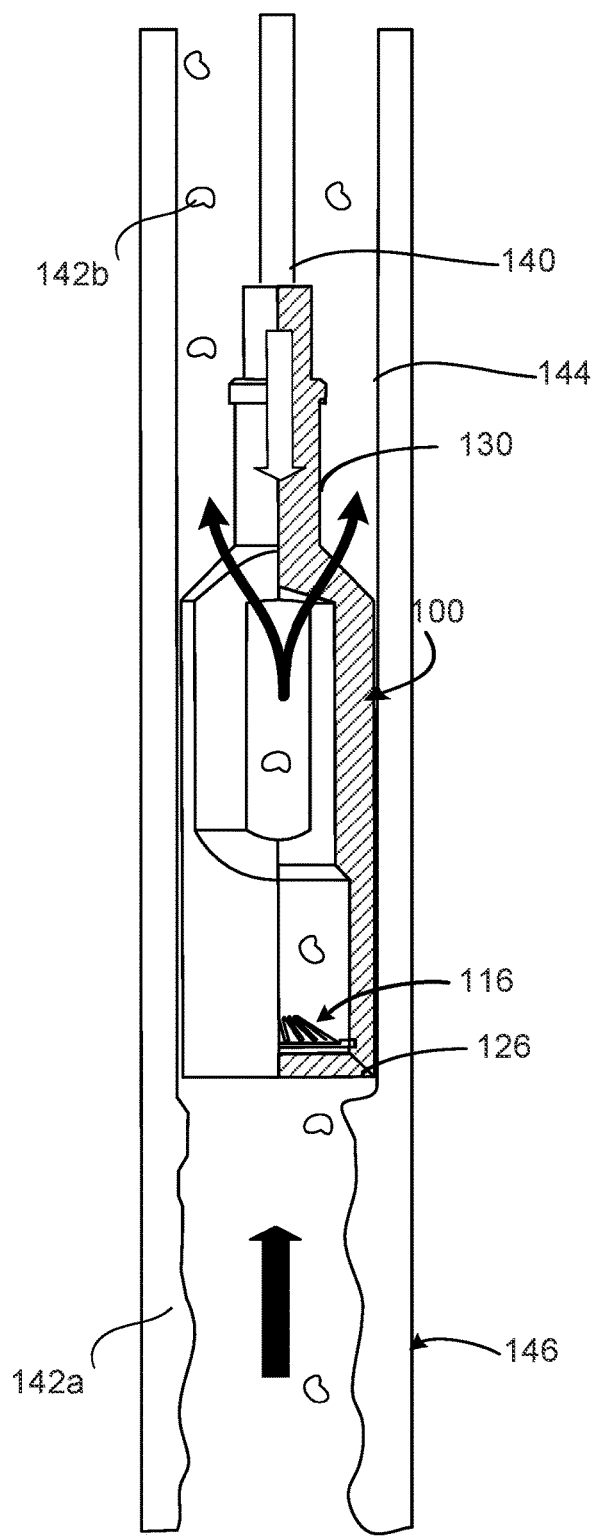
FIGS. 4A-4C are front views of the wellbore gauge cutter apparatus of FIG. 1 in operation.
Figure 4B:
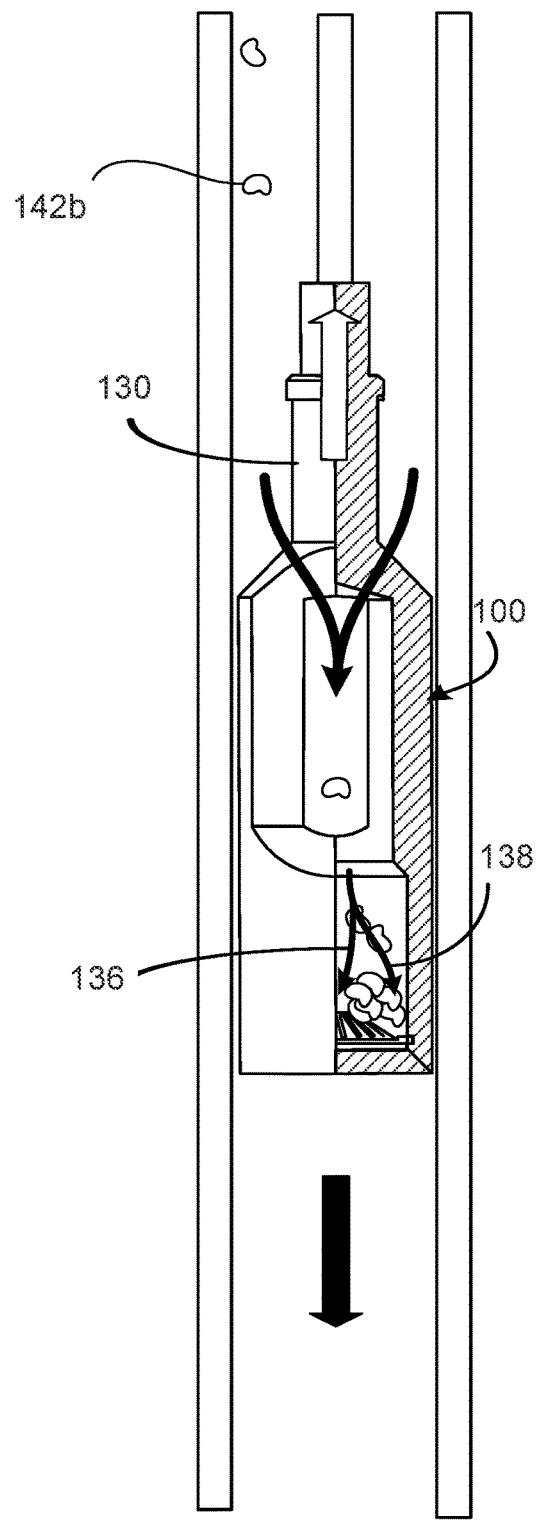
Figure 4C:
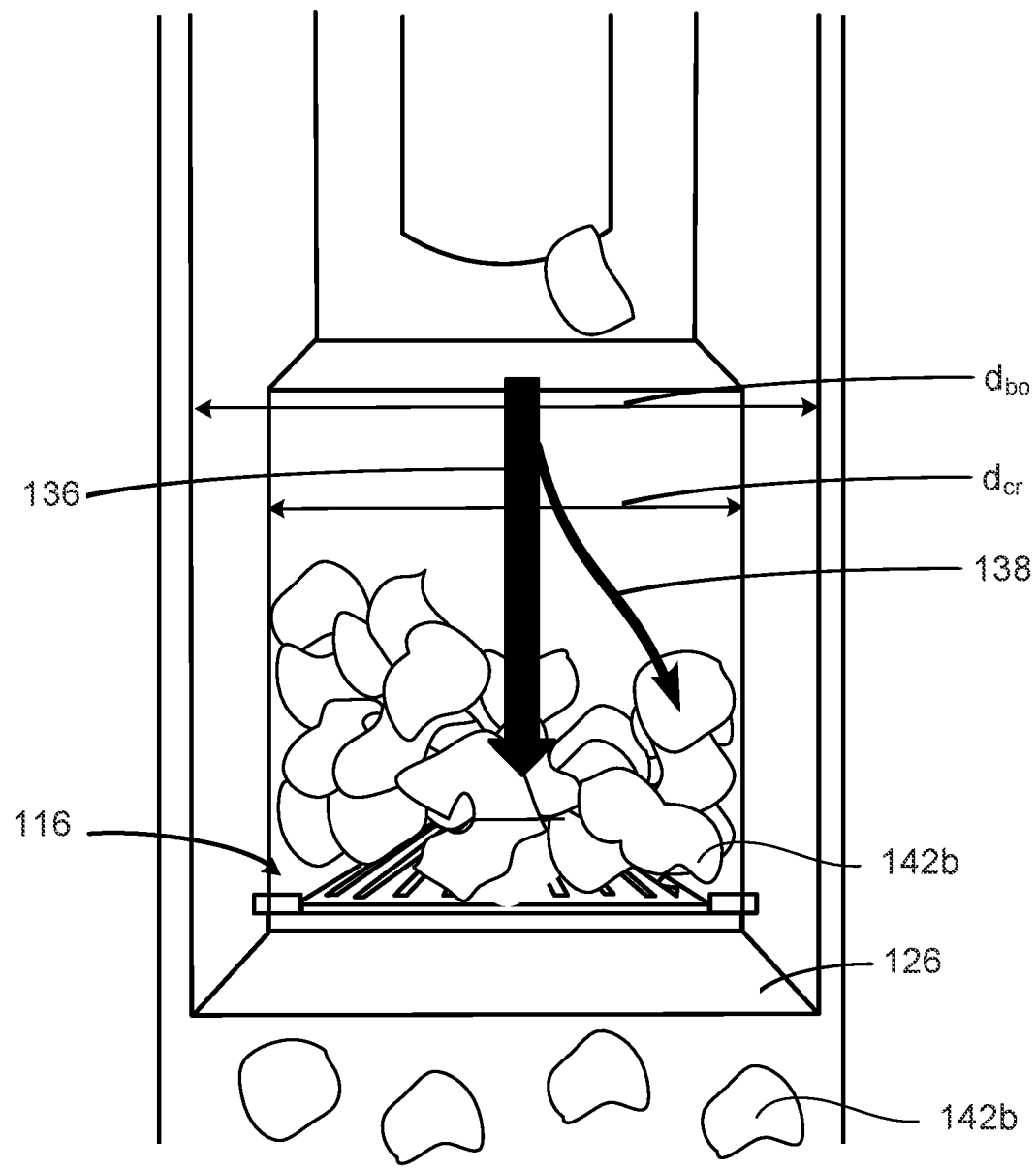

The sampling body 102 has an external diameter $d_{bo}$ (FIG. 4C). The central recess 104 of the sampling body 102 also has a diameter $d_{cr}$ (FIG. 4C) and a cross sectional area $A_{cr}$. The cross sectional area $A_{ca}$ of the central recess 104 is circular, but however, the cross section of other central recesses may be a different shape, for example, annular, crescent, half circle, square, triangular, polygonal, or any other shape.

The cross sectional areas $A_{sc}$, $A_{cr}$ of the sample collector 116 and the central recess 104 are taken at the same axial location in the central recess 104. The cross sectional area $A_{sc}$ of the sample collector 116 is less than the cross sectional area $A_{cr}$ of the central recess 104 (e.g., less than half), because the sample collector 116 only extends into a part of the central recess 104, not across the entire central recess 104. The ratio of the cross sectional area $A_{sc}$ of the sample collector 116 to the cross sectional area $A_{cr}$ of the central recess 104 can be, for example, 1:8, 1:6, 1:4, 1:3, 1:2, 2:3, 3:4, 4:5, 5:6, 6:7, 7:8, 8:9, or 9:10.

This configuration forms two flow paths in the central recess 104. A first flow path 136 (FIG. 4B) and a second flow path 138 (FIG. 4B). The first flow path 136 extends between the inlet 106 and the outlet 110 and does not interact with the sample collector 116. The second flow path 138 extends between the inlet 106 and the outlet 110 via the sample collector 116 so that the particles and fluid flowing in the second flow path 138 are filtered by the sample collector 116.

FIGS. 4A-4C are front views of the wellbore gauge cutter apparatus 100 in operation. FIG. 4A shows the wellbore gauge cutter apparatus 100 during RIH operation. The wellbore gauge cutter apparatus 100 is moved downhole by the extension of a slickline 140. The gauge cutter 126 cuts debris 142a from an internal wall 144 of a wellbore casing 146. The cut or dislodged debris 142a forms particles 142b that are suspended in the fluid in the casing 146. The fluid moves uphole relative to the wellbore gauge cutter apparatus 100 moving downhole. Particles 142b are not collected in the sample collector 116 as the wellbore gauge cutter apparatus 100 moves downhole.

FIG. 4B is a front view of the wellbore gauge cutter apparatus 100 during POOH operation. The wellbore gauge cutter apparatus 100 is moved uphole by the retraction of the slickline 140. The fluid and particles 142b in the casing move downhole relative to the wellbore gauge cutter apparatus 100 moving uphole. The fluid and particles 142b in the central recess 104 are divided into the first flow path 136 and the second flow path 138. A first portion of the fluid and particles 142 flows through the first flow path 136. A second portion of the fluid flows the second flow path 138. The first and second portion of fluid, together, form the total fluid flow in the central recess 104. In some instances, the first and second flow paths are merged from the inlet 106 to an uphole edge of the sample collector.

The fluid and particles 142b in the first flow path 136 enter the inlet 106, bypass the sample collector 116, and exit the outlet 110. The fluid and particles 142b in the first flow path 136 do not interact with the sample collector 116. The fluid and particles 142b in the second flow path 138 enter the inlet 106 and are separated by the sample collector 116. Particles 142b of a minimum size are retained in the sample collector 116. After separation (e.g., sampling, filtering), the fluid and particles 142 less than the minimum particle size of the sample collector 116 exit the outlet 110.

In some instances first portion of the fluid is larger than the second portion of the fluid, so that the first flow path is larger than the second flow path. In some instances, the second portion of the fluid is larger than the first portion of the fluid, so that the second flow path is larger than the first flow path. Regardless, as the sample collector 116 holds more particles 142b less fluid can flow through the second flow path 138. As a result, over time, the second portion of the fluid can decrease while the first portion of the fluid increases. In some cases, when the sample collector is full, the all fluid in the central recess flows through the first flow path.

The sample collector 116 retains a small portion of the total number or particles present in the fluid, for example a particle weight of at least 100 grams (e.g. 50 grams to 1000 grams).

FIG. 4C shows a close view of the sample collector 116 in FIG. 4B. The sample collector 116 retains particles 142b and has a volume of about 0.3 liters to about 1 liter (e.g., 0.5 liters to 0.75 liters). Some sample collectors have a volume between 0.1 liters and 1.5 liters, inclusive. The particles may include wax particles, formation fine particles, scale particles (e.g., $CaCO_3$, $NaCl$, $BaSO_4$, $Sr_2SO_4$, $FeS$), corrosion particles, metal particles, or a combination thereof.

Figure 5:
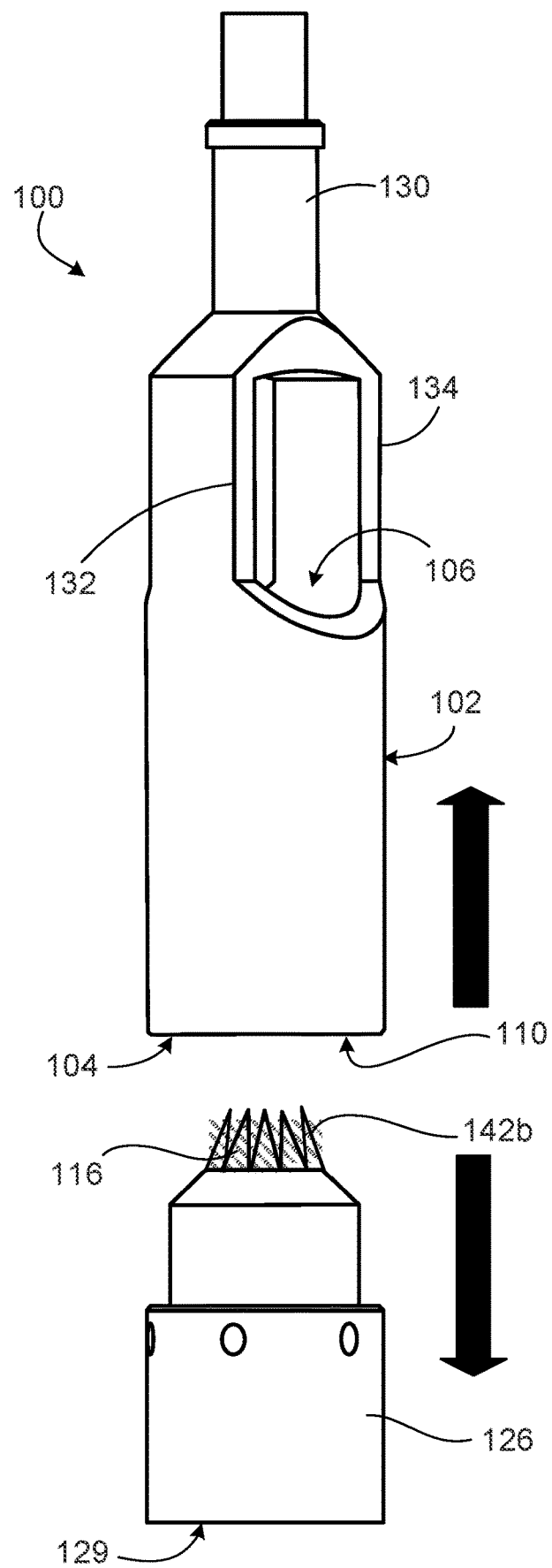
FIG. 5 is a front view of the sampling body of the wellbore gauge cutter apparatus from a sample collector of the wellbore gauge cutter apparatus of FIG. 1 during sample removal.

FIG. 5 is a front view of the sampling body 102 of the wellbore gauge cutter apparatus 100 during sample removal. The sample collector 116 is removable or separable from the sampling body 102. In the separated state, the collected sample of particles 142b are easily accessible for further testing in a lab. The order in which the particles 142b were collected may also preserved. In some instances, if the ordering of collection is known, a depth or position of the particles, or type of particle, can be determined.

Figure 6:
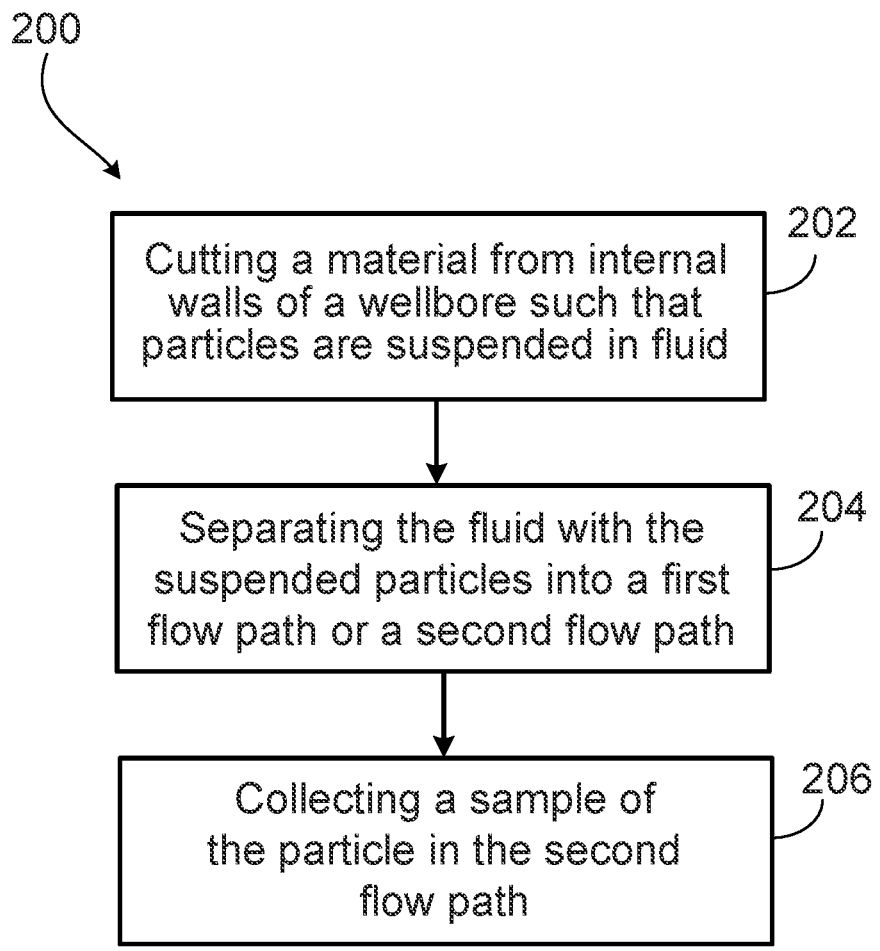
FIG. 6 is a flow diagram of an example of a method for using a gauge cutter apparatus.

FIG. 6 is a flow diagram of an example of a method 200 for using a gauge cutter apparatus. The method is described with reference to gauge cutter apparatus 100, however, the method may be used with any application apparatus described herein or known in the art.

The method includes connecting the wellbore gauge cutter apparatus 100 to a slickline 140 and inserting the wellbore gauge cutter apparatus 100 into a wellbore casing 146 containing fluid and debris on the internal wall 144 of the casing 146. Next, the method 200 includes moving the gauge cutter 126 during a downhole motion of the wellbore gauge cutter apparatus 100 through the casing 146 of the wellbore, thereby cutting debris 142a (material) from the internal walls 144 of the casing 146 of the wellbore. The particles 142b of the debris (material) 142a are suspended in fluid. (Step 202). The wellbore gauge cutter apparatus 100 continues cutting debris 142a from the internal walls 144 of the casing 146. The downhole cutting motion eventually cuts the entire casing, or predetermined length of debris (material) 142a from the casing 146.

After cutting the debris (material) 142a from the internal walls 144, the wellbore gauge cutter apparatus 100 is moved uphole thereby sampling a portion of the particles 142b in the fluid. The method includes moving the gauge cutter apparatus 100 uphole, thereby separating, by the sampling collector 116 mechanically connected to the gauge cutter 126, the fluid with the suspended particles 142b in the sampling body 102 of the wellbore gauge cutter apparatus 100 into a first flow path 136 of the sampling body 102 or a second flow path 138 of the sampling body 102. In some cases, a majority of the fluid entering the sampling body 102 is separated into the first flow path 136 of the sampling body 102. (Step 204).

Next, the wellbore gauge cutter apparatus 100 collects a sample of the particles 142b with the sampling collector 116 (screen or membrane) arranged in the second flow path 138 of the sampling body 102. (Step 206).

The wellbore gauge cutter apparatus 100 continues to move uphole as the sampling collector 116 fills with particle 142b. The sample collector 116 may fill to a maximum volume, at which time, no or small amounts of fluid can flow in the second flow path 138. When the sample collector 116 is full, a majority (or all) of the fluid in the sampling body 102 flows through the first flow path 136.

The wellbore gauge cutter apparatus 100 reaches the surface and may be taken to a lab or analysis station to analyze the particles 142b collected in the sample collector 116. In these settings, the sampling body 102 is disconnected from the sample collector 116 and sample collector (e.g., a membrane) is removed from the sampling body to access the collected particles 142. The method further includes analyzing the particles using X-ray Diffraction (XRD) and/or an acid test.

Figure 7:
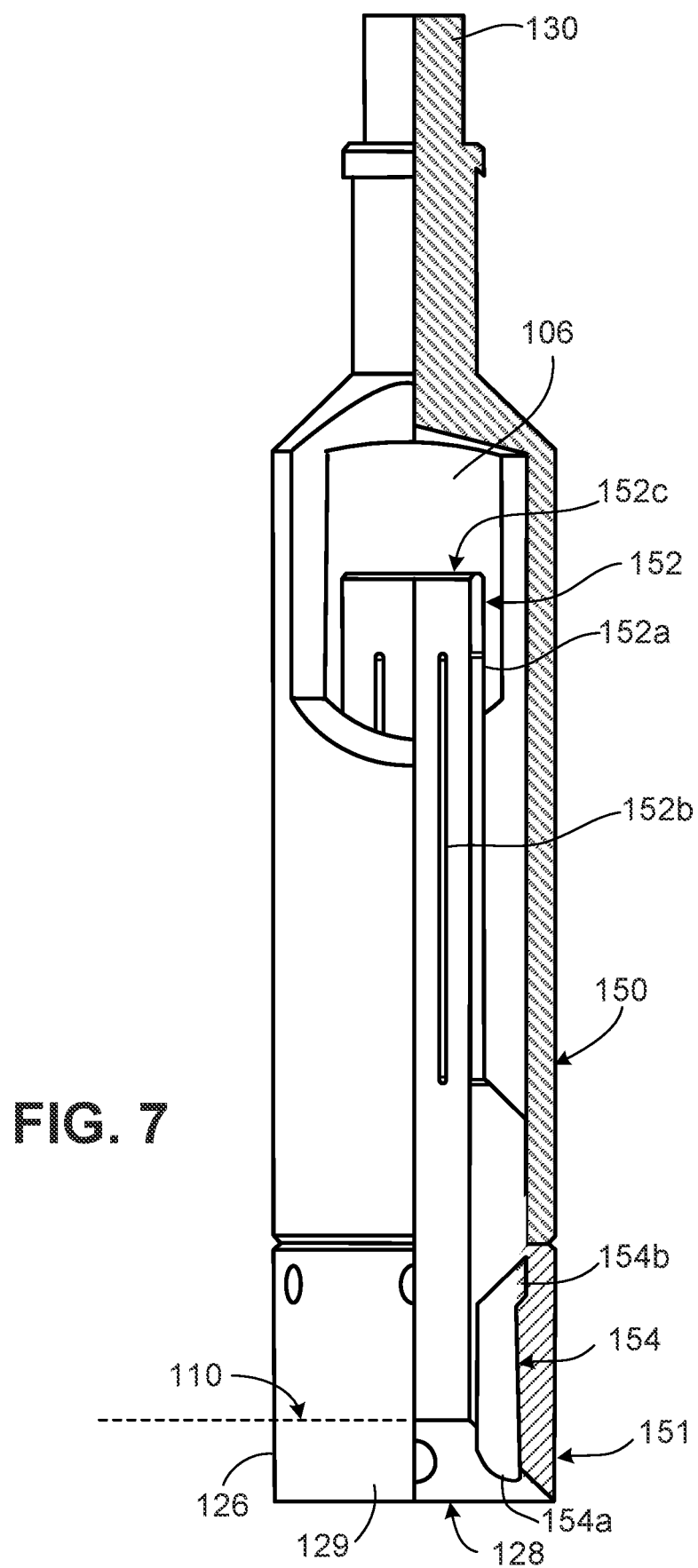
FIG. 7 is a front view of a wellbore gauge cutter apparatus with an alternative embodiment of a gauge cutter, a first sample collector, and a second sample collector.

FIG. 7 is a front view of a wellbore gauge cutter apparatus 100 with an alternative embodiment of a gauge cutter 151, a first sample collector 152, and a second sample collector 154. The sample collector 152 is substantially similar to the sample collector 116, however, the sample collector 152 is a hollow cylindrical divider (body) 152a having slots 152b and a central aperture 152c. The sample collector 152 is arranged concentrically within the sampling body 102 and extends from the outlet 110 to the inlet 106 so that the fluid entering the sampling body 102 is divided between first and second flow paths 156, 158 upon entering the sampling body 102.

The first flow path 156 is defined in the central aperture 152c of the sample collector 152. The second flow path 158 is defined between the inner wall 114 of the sampling body 102 and an outer wall of the cylindrical divider 152a. The first and second flow paths 156, 158 extend from the inlet 106 to the outlet 110 of the sampling body 102.

The gauge cutter 151 of the wellbore gauge cutter apparatus 100 is substantially similar to gauge cutter 126, however, the gauge cutter 151 includes a sample inlet 154a that extends to a second sample collector 154 arranged in gauge cutter 151. In this configuration, the wellbore gauge cutter apparatus 100 collects samples when performing RIH and POOH operations (moving downhole and uphole). The gauge cutter 151 also includes a sample outlet 154b. During operation the sample outlet 154b is covered by the sampling body 102. In some cases, the sample outlet is exposed during operation.

Figure 8A:
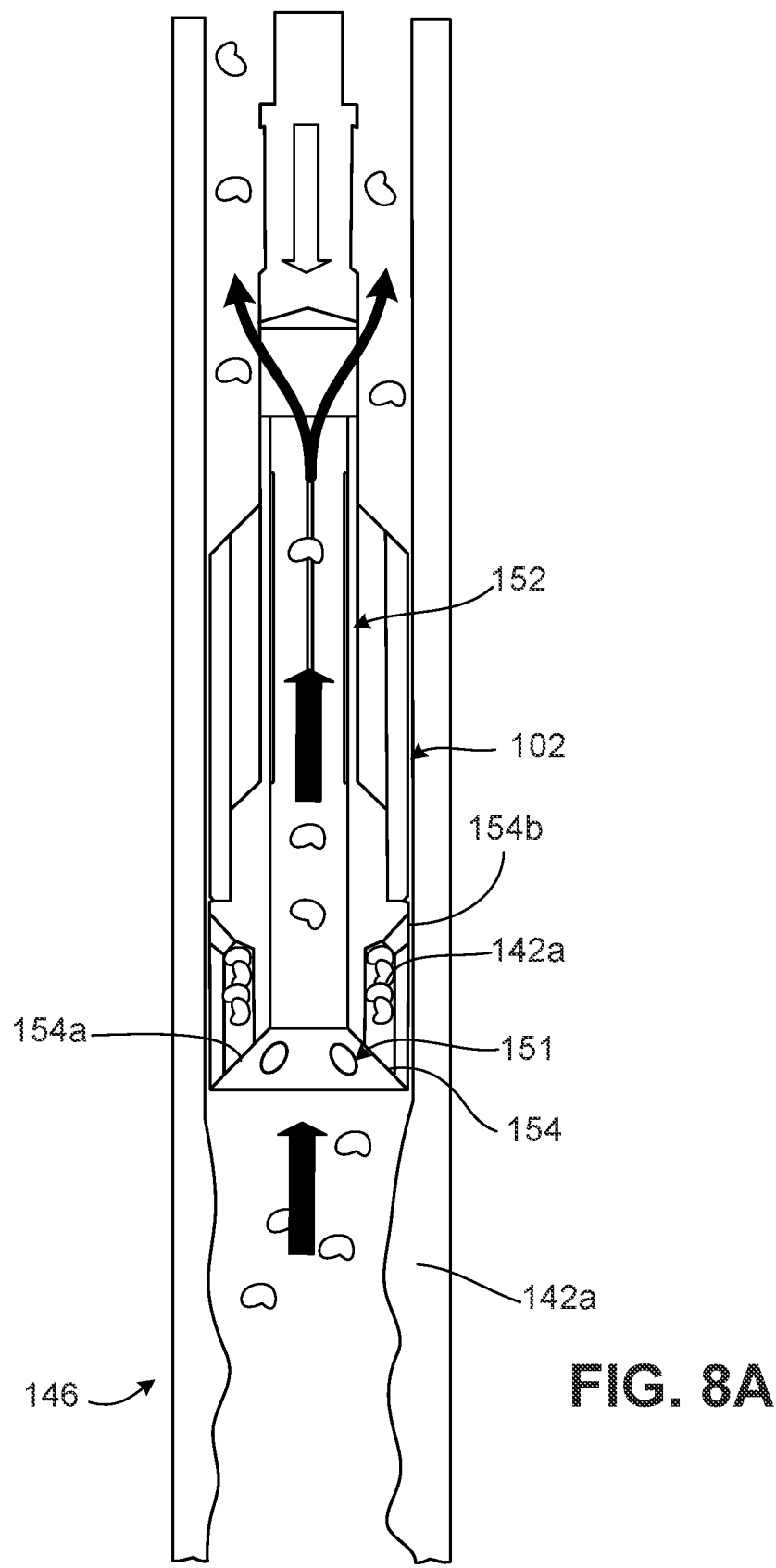
FIGS. 8A and 8B are front views of the wellbore gauge cutter apparatus having the gauge cutter, first sample collector, and second sample collector, in operation
Figure 8B:
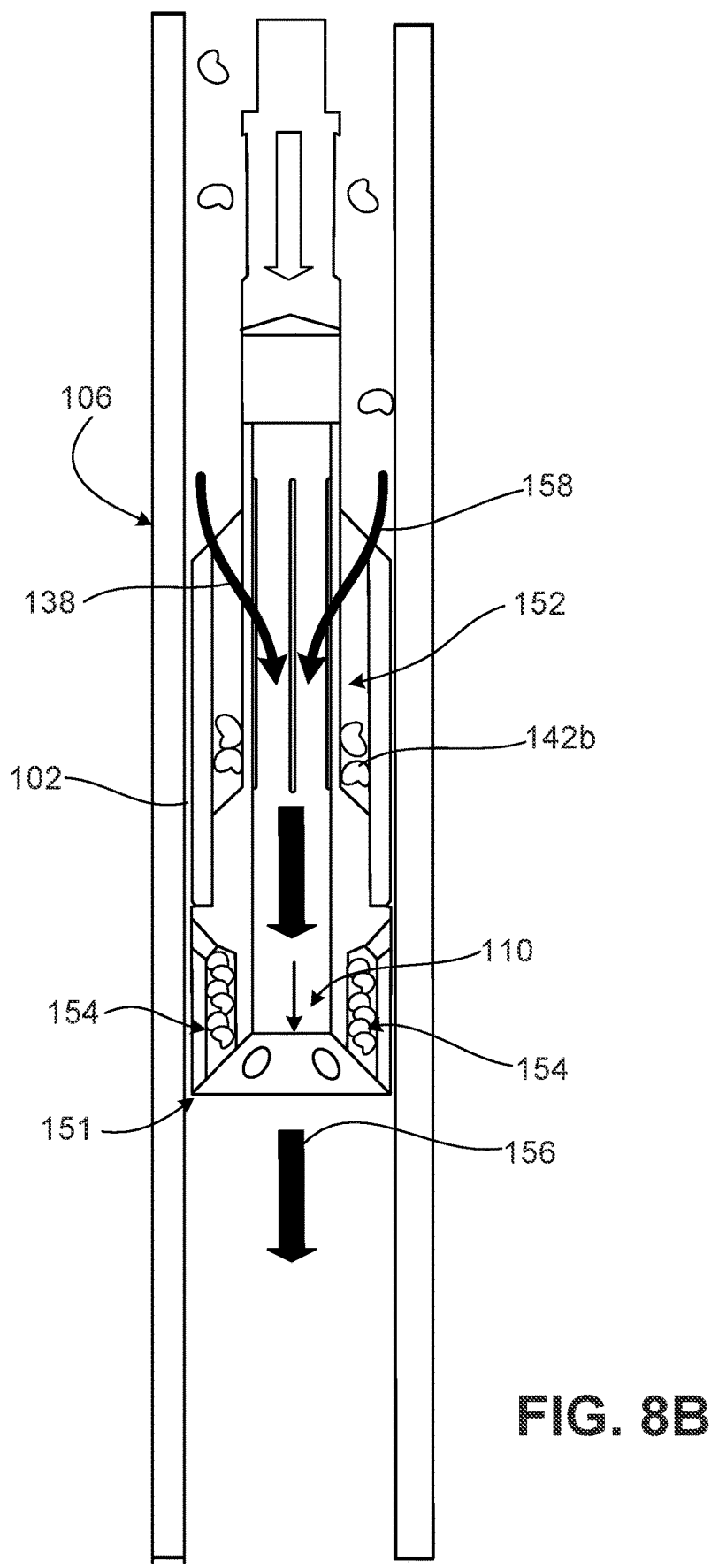

FIGS. 8A and 8B are front views of the wellbore gauge cutter apparatus 100 having the gauge cutter 151, first sample collector 152, and second sample collector 154 in operation. FIG. 8A is a cross section front view of the wellbore gauge cutter apparatus 100 cutting the debris 142a from the casing 146. The wellbore gauge cutter apparatus 100 moves downhole (RIH operation) to cut the debris 142a from the internal wall 144 of the casing 146. A portion of the debris 142a is directed into the sample inlet 154a arranged on the free end 128 of the gauge cutter 151. The debris 142a enters the sample inlet 154a and is held in the second sample collector 154. Further movement downhole, moves the collected debris 142a in the sample collector 154 towards the covered sample outlet 154b of the sample collector 154. Some of the dislodged debris 142a forms particles 142b in the fluid.

In FIG. 8B, the wellbore gauge cutter apparatus 100 moves uphole (POOH operation) and begins to collect samples of the particles 142b in the fluid. The fluid and particles 142b are divided into the first flow path 156 and the second flow path 158. The fluid and particles 142b diverted into the second flow path 158 are separated by the sample collector 152 and a portion of the particles 143b are retained in the sample collector 152. The fluid and small particles 142b that passed through the sample collector 152 exit the sampling body 102 via the outlet 110. The fluid and particles 142b that enter the first flow path 156 at the inlet 106 do not interact with the sample collector 152 and exit the outlet 110, unfiltered. A small sample of particles 142b and debris 142a is collected using the first sample collector 152 and second sample collector 154.

Figure 9A:
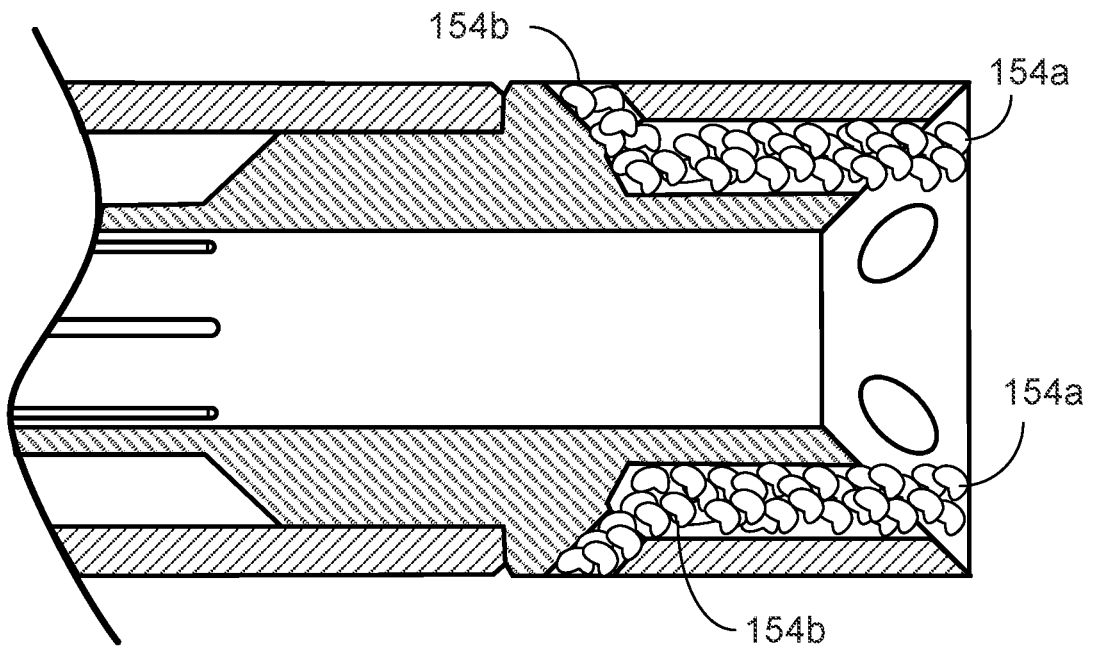
FIGS. 9A and 9B are cross-sectional views of the second sample collector of the wellbore gauge cutter apparatus during sample removal.
Figure 9B:
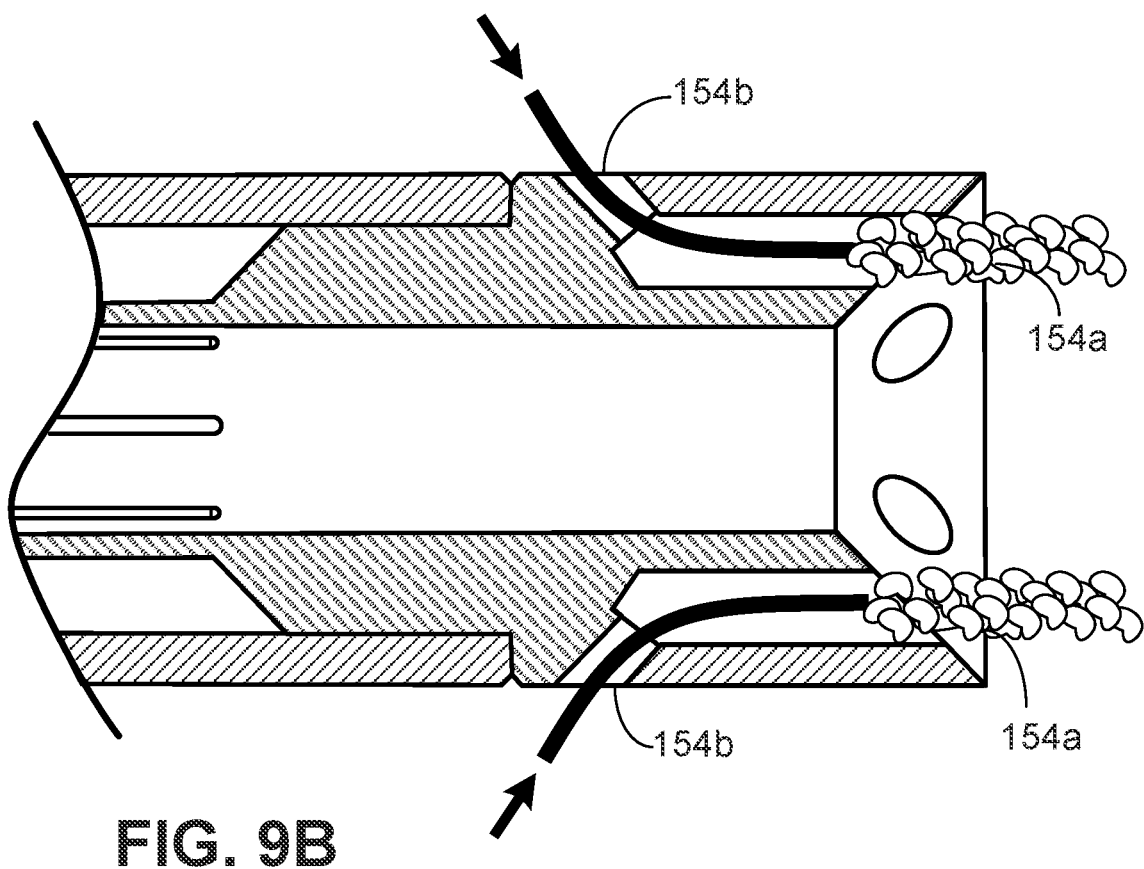

FIGS. 9A and 9B are cross-sectional views of the second sample collector 154 of the wellbore gauge cutter apparatus 100 during sample removal. The first and second sample collectors 152, 154 are separable from the sample body 102. Separating the sample collectors 152, 154 from the sample body 102 exposes the sample outlet 154b of the second sample collector. To extract the sample of debris 142a, a pipe can be inserted into the sample outlet 154b and can press on the collected debris 142a to move the debris 142a through the sample inlet 154a. The collected debris samples from the first and second sample collectors 152, 154 can then be analyzed using techniques known in the art.

FIG. 10 is a perspective view of a wellbore gauge cutter apparatus 100 having a removable sampling body 102 and a gauge cutter 160. The gauge cutter 160 is substantially similar to the gauge cutter 126, however, the gauge cutter 160 has a gauge body 162, a blade 164, and a gauge connector 166 that connects to the sampling body 102 to the gauge cutter 160. The gauge connector 166 connects to a protrusion 168 of the sampling body 102 extending from the second end 112 of the sampling body 102. The gauge connector 166 and protrusion 168 have a snap fit connection, however, the gauge connector and protrusion may be connected by any suitable connection. The gauge cutter 160 is spaced axially from the sampling body 102 by the gauge connector 166 and protrusion 168. The aperture 129 that extends through the gauge cutter 160 has a gauge inlet 170 and a gauge outlet 172 that are open to the environment.

Figure 11:
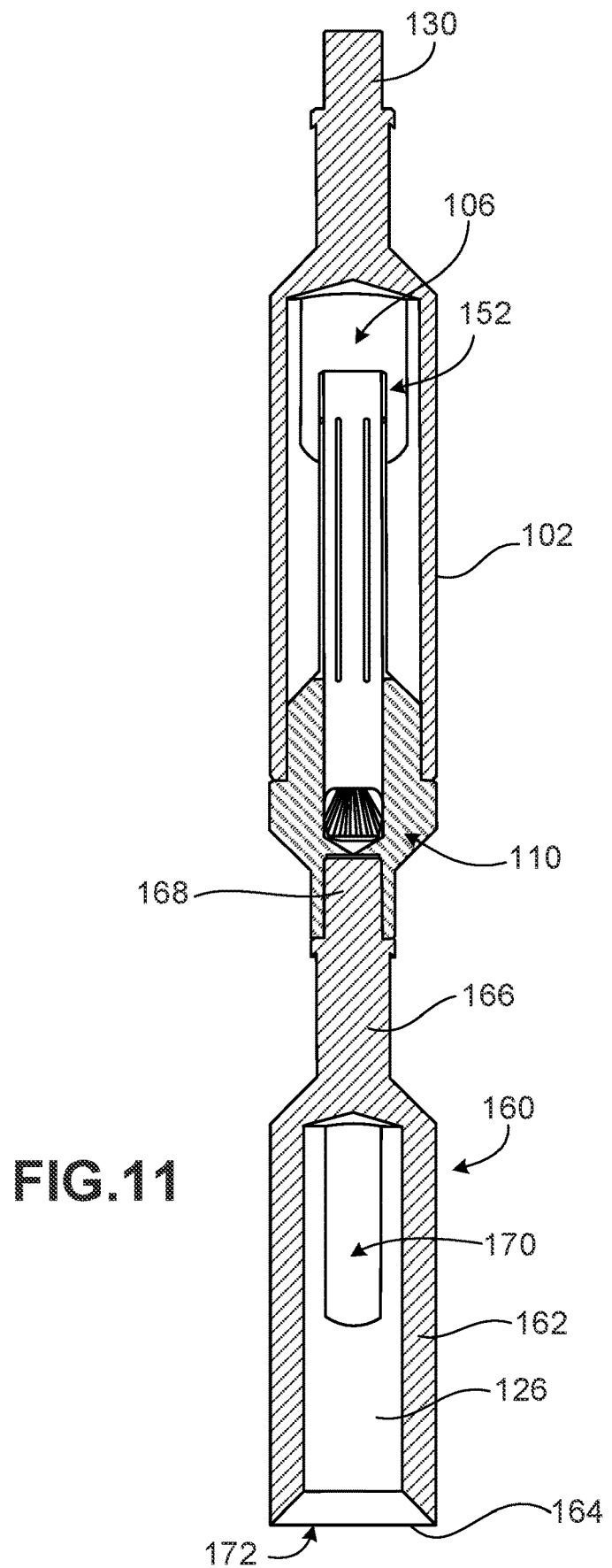
FIG. 11 is a cross sectional front view of the gauge cutter apparatus of FIG. 10.

FIG. 11 is a cross-sectional view of the wellbore gauge cutter apparatus 100 having the gauge cutter 160 axially spaced from the sampling body 102. The sampling body 102 and sampling collector 154 are connected such that fluid flows into the inlet 106 of the sampling body 102 and exits the outlet 110 of the sampling body 102 via either the first flow path 156 or second flow path 158 during POOH operation. The fluid containing particles 142b then enters the gauge inlet 170 and exits the gauge outlet 172 via the aperture 129 of the gauge cutter 160. The gauge cutter 160 has an outer diameter $d_{gc}$ (FIG. 3), which is sized such that the gauge cutter 160 cuts debris 142a from an internal wall 144 of a wellbore casing 146. The diameter $d_{gc}$ (FIG. 3) of the gauge cutter 160 and the outer diameter $d_{bo}$ of the sample body 102 (FIG. 4C) are equal, however, in some cases, the diameter of the gauge cutter is larger than the outer diameter of the sample body. In some instances, the gauge cutter 160 can be disconnected from the sampling body 102 and replaced with a new gauge cutter 160. In some instances, the gauge cutter is replaced due to wear. In some instances the gauge cutter is replaced with a gauge cutter of equal or greater diameter. In some instances, the gauge cutter is replaced with a gauge cutter of a different shape.

Figure 12:
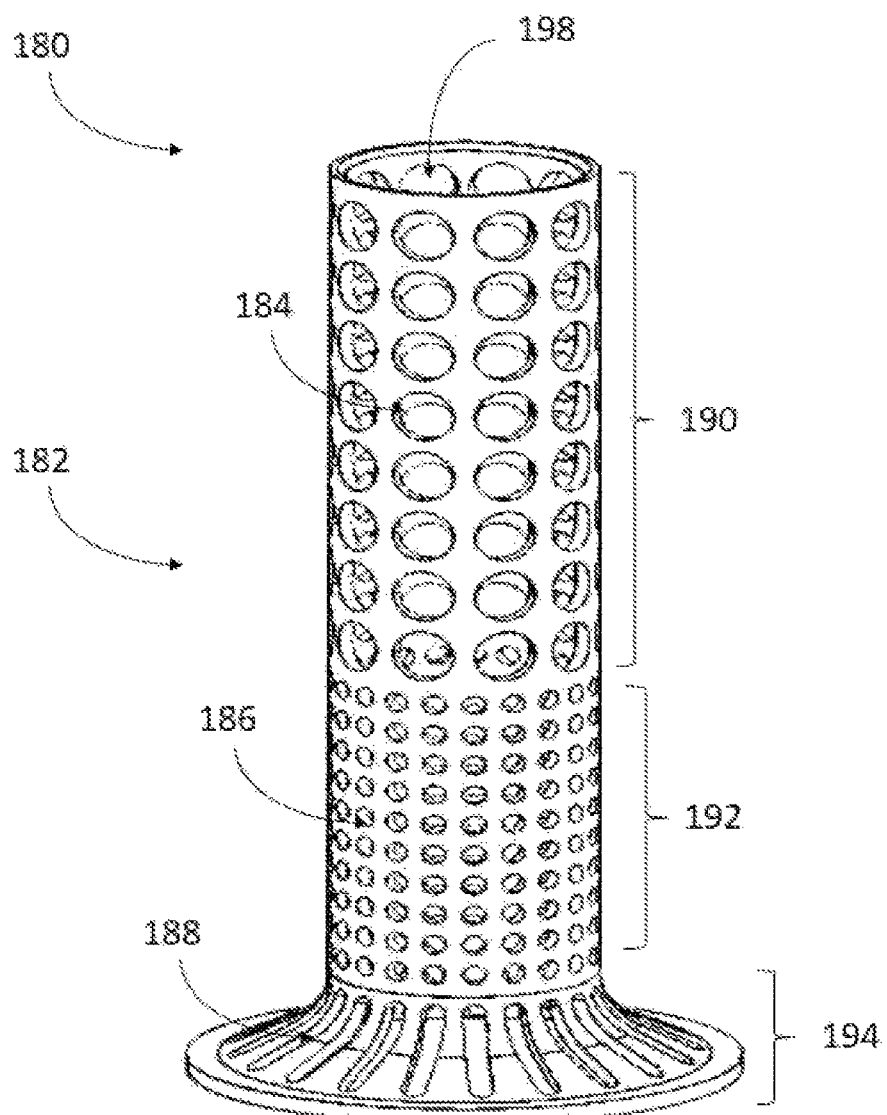
FIG. 12 is a front view of a sample collector with apertures of various sizes.

FIG. 12 is a front view of a sample collector 180 having apertures 182 of various sizes. The sample collector 180 is substantially similar to the sample collector 152, however, the sample collector 180 includes three types of apertures 182. The apertures 182 include first apertures 184 having a first width, second apertures 186 having a second width, and third apertures 188 having a third width. The width of the third apertures 188 is equal to the width of the second apertures 186. The width of the first apertures 184 is larger than the widths of the first and second apertures 186, 188.

The sample collector 180 has a first (uphole) portion 190, a second portion 192, and a third (downhole) portion 194. The second portion 192 extends between the first portion 190 and the third portion 194. The first apertures 184 are arranged in the first portion 190. The second apertures 186 are arranged in the second portion 192. The third apertures 188 are arranged in the third portion 194. In this configuration, the second and third portions 192, 194 of the sample collector 180 hold smaller particles than the first portion 190 of the sample collector 180, thereby forming a gradient filter. The sample collector 180 with a gradient filter is able to retain a range of particle sizes, e.g., large particles and small particles. As the sample collector 180 fills with particles, the minimum particle size changes. Therefore, small and large particles may initially be sampled, however, as the volume of particles in the sample collector 180 increases, only large particles are retained and smaller particles may flow through sample collector 180.

In the sample collector 180, the first apertures 184 are circular holes, the second apertures are circular holes, and the third apertures are slots, however, in other sample collectors the first, second, and third apertures may be shaped differently. In some sample collectors, the first, second, and third apertures are the same shape. In some sample collectors, the first, second, and third apertures are each different shapes.

In use, fluid and particles flow through the first flow path in a central aperture 198 of the sample collector 180 or flow through a second flow path. The fluid and particle flowing in the second flow path interacts with the sample collector 180. First, the third portion 194 of the sample collector 180 filters the fluid and particles, retaining only particles that are larger than the width of the third apertures 188. As more particles are gathered, the third portion 194 of the sample collector 180 fills. The fluid and particles then flow through the second apertures 186, so that the sample collector retains only particles larger than the width of the second apertures 186. As more particles are gathered, the second portion 192 of the sample collector 180 fills. The widths of the second and third apertures 186, 188 are equal, therefore, the minimum retained particle size of the second and third portions 192, 194 are the same.

Once the second portion 192 is filled, the fluid and particles then flow through the first apertures 184, so that the sample collector retains only particles larger than the width of the first apertures 184. The width of the first apertures 188 is larger than the second and third apertures 186, 188, therefore, the minimum retained particle size in the first portion is larger than the minimum retained particle size of the second and third portions 192, 194.

The gauge cutter apparatus is removed, the sample collector 180 is retrieved and the collected particles are examined.

While the sample collector 180 has been described as having apertures that decrease in width from the first portion of the sample collector to the third portion of the sample collector, the apertures may also increase in width the first portion of the sample collector to the third portion of the sample collector. Some sample collectors include two portions. Some sample collectors include more than three portions, for example, 4, 5, or 6 portions, each with apertures of a specified width.

In some sample collectors, the first, second, and third portions are made of different material, for example, the third portion may be a rigid membrane, the second portion may be a flexible fabric, and the first portion may be a polymer membrane. In some embodiments, the first, second, and third portions are releasably attached to each other, so that the sample collector may be altered to fit different wellbores or particle types.

A number of embodiments have been described. Nevertheless, it will be understood that various modifications may be made without departing from the spirit and scope of the disclosure. Accordingly, other embodiments are within the scope of the following claims.

What is claimed is:

1. A wellbore gauge cutter apparatus comprising:
an uphole end;
a downhole end;
a cylindrical body defining a central recess extending from a first end of the cylindrical body to a second end of the cylindrical body,
a cutter blade connected to the second end of the cylindrical body;

a first sample collector permeable to fluids and configured to retain particles, the first sample collector arranged in the central recess of the cylindrical body; wherein the central recess of the cylindrical body has a first cross-section having a first area, wherein the first sample collector has a second-cross section having a second area, wherein the second area is less than the first area; and a second sample collector arranged in the cutter blade, wherein the second sample collector comprises a sample inlet and a sample outlet; wherein the sample outlet of the second sample collector is covered by the cylindrical body.

2. The wellbore gauge cutter apparatus according to claim 1, wherein the cylindrical body comprises a first beam extending from the first end of the cylindrical body to a connector.

3. The wellbore gauge cutter apparatus according to claim 2, wherein the cylindrical body comprises a second beam extending from the first end of the cylindrical body to a connector, wherein the first beam and second beam define a body inlet, wherein the body inlet is in fluid communication the central recess of the cylindrical body.

4. The wellbore gauge cutter apparatus according to claim 1, wherein the first sample collector has a volume of about 0.3 liters to about 1liter.

5. The wellbore gauge cutter apparatus according to claim 1, wherein the first sampling collector comprises a membrane permeable to fluids.

6. The wellbore gauge cutter apparatus according to claim 5, wherein the first sampling collector is releasable from the cylindrical body.

7. The wellbore gauge cutter apparatus according to claim 5, wherein the first sample collector is annularly shaped.

8. The wellbore gauge cutter apparatus according to claim 5, wherein the first cross-section is circular.

9. The wellbore gauge cutter apparatus according to claim 5, wherein the cutter blade is a gauge cutter.

10. The wellbore gauge cutter apparatus according to claim 1, wherein the first sample collector is mounted to the cylindrical body.

11. The wellbore gauge cutter apparatus according to claim 1, wherein cutter blade extends from a connection between the cutter blade and the second end of the body, to a free end, wherein the inlet of the second sample collector is arranged in the cutter blade at the free end of the cutter blade.

12. A wellbore gauge cutter apparatus comprising:
an uphole end;
a downhole end;
a cylindrical body defining a central recess extending from a first end of the cylindrical body to a second end of the cylindrical body,
a cutter blade connected to the second end of the cylindrical body;
a first sample collector permeable to fluids and configured to retain particles, the sample first collector arranged in the central recess of the cylindrical body; and
a second sample collector arranged in the cutter blade; wherein the first sample collector comprises:
a first portion having first apertures with a first diameter,
a second portion having second apertures with a second diameter, and
a third portion, wherein the second portion is arranged between the first portion and the third portion.

13. The wellbore gauge cutter apparatus according to claim 12, where in the first diameter is greater than the second diameter.

14. The wellbore gauge cutter apparatus according to claim 12, wherein third apertures are defined in the third portion having a third width; wherein the second diameter is greater than the third width.

15. The wellbore gauge cutter apparatus according to claim 12, wherein the second sample collector comprises a sample inlet.

16. The wellbore gauge cutter apparatus according to claim 15, wherein the second sample collector comprises a sample outlet.

17. The wellbore gauge cutter apparatus according to claim 16, wherein the central recess of the cylindrical body has a first cross-section having a first area, wherein the first sample collector has a second-cross section having a second area, wherein the second area is less than the first area.

18. A wellbore gauge cutter apparatus comprising:
an uphole end;
a downhole end;
a cylindrical body defining a central recess extending from a first end of the cylindrical body to a second end of the cylindrical body,
a cutter blade connected to the second end of the cylindrical body;
a first sample collector permeable to fluids and configured to retain particles, the sample first collector arranged in the central recess of the cylindrical body, the first sample collector comprising:
a first portion,
a second portion, and
a third portion, wherein the second portion is arranged between the first portion and the third portion; and
a second sample collector arranged in the cutter blade, wherein the second sample collector comprises a sample inlet and a sample outlet; wherein the sample outlet of the second sample collector is covered by the cylindrical body.

19. The wellbore gauge cutter apparatus according to claim 18, wherein cutter blade extends from a connection between the cutter blade and the second end of the body, to a free end, wherein the inlet of the second sample collector is arranged in the cutter blade at the free end of the cutter blade.

20. The wellbore gauge cutter apparatus according to claim 18, wherein the cylindrical body comprises a first beam extending from the first end of the cylindrical body to a connector.

21. The wellbore gauge cutter apparatus according to claim 20, wherein the cylindrical body comprises a second beam extending from the first end of the cylindrical body to a connector, wherein the first beam and second beam define a body inlet, wherein the body inlet is in fluid communication the central recess of the cylindrical body.

22. The wellbore gauge cutter apparatus according to claim 18, wherein the first sample collector has a volume of about 0.3 liters to about 1 liter.

23. The wellbore gauge cutter apparatus according to claim 18, wherein the first sampling collector comprises a membrane permeable to fluids.

24. The wellbore gauge cutter apparatus according to claim 23, wherein the first sampling collector is releasable from the cylindrical body.

25. The wellbore gauge cutter apparatus according to claim 23, wherein the first sample collector is annularly shaped.

26. The wellbore gauge cutter apparatus according to claim 23, wherein the cutter blade is a gauge cutter.

27. The wellbore gauge cutter apparatus according to claim 18, wherein the first sample collector is mounted to the cylindrical body.

28. The wellbore gauge cutter apparatus according to claim 18, wherein first apertures are defined in the first portion having a first diameter and second apertures are defined in the second portion having a second diameter.

29. The wellbore gauge cutter apparatus according to claim 28, where in the first diameter is greater than the second diameter.

30. The wellbore gauge cutter apparatus according to claim 28, wherein third apertures are defined in the third portion having a third width; wherein the second diameter is greater than the third width.

* * * * *